United States Patent [19]
Still et al.

[11] Patent Number: 5,599,926
[45] Date of Patent: Feb. 4, 1997

[54] $A_4B_6$ MACROTRICYCLIC ENANTIOSELECTIVE RECEPTORS FOR AMINO ACID DERIVATIVES, AND OTHER COMPOUNDS

[75] Inventors: W. Clark Still, New York, N.Y.; Julian A. Simon, Cambridge, Mass.; Shawn D. Erickson, Strasbourg, France; Seung S. Yoon, New York, N.Y.; Jong-In Hong, Seoul, Rep. of Korea

[73] Assignee: The Trustees of Columbia University in the City of New York, New York, N.Y.

[21] Appl. No.: 188,146

[22] Filed: Jan. 27, 1994

Related U.S. Application Data

[63] Continuation-in-part of Ser. No. 901,401, Jun. 19, 1992, Pat. No. 5,342,934.
[51] Int. Cl.[6] .................... C07D 487/18; C07D 513/18; C07D 498/18
[52] U.S. Cl. ............................ 540/456; 540/460; 560/25
[58] Field of Search ..................................... 540/456, 460

[56]                References Cited

U.S. PATENT DOCUMENTS

| 4,043,979 | 8/1977 | Cram | 260/47 |
| 4,128,556 | 12/1978 | Cram | 546/26 |

OTHER PUBLICATIONS

Diederich, F., Complexation of Neutral Molecules by Cyclophan Hosts, *Angew. Chem. Int. Ed. Engl.*, 27:362–386 (1988); Germany.
Ebmeyer, F., and Vogtle, F., Selective Molecular Recognition of Trihydroxybenzenes, *Angew. Chem. Int. Ed. Engl.*, 28:79–81 (1989); Germany.
Fujita, T., and Lehn, J.–M., Synthesis of Dome–Shaped Cyclophane Type Macrotricyclic Anion Receptor Molecules, *Tetrahedron Letters*, 29 (14):1709–1712 (1988); Great Britain.
Garrett, T. M., et al., Synthesis and Characterization of Macrobicyclic Iron (III) Sequestering Agents, *J. Am. Chem. Soc.*, 113 (13):2965–2977(1991); U.S.A.
Hong, J.–I., et al., Highly Selective Binding of Simple Peptides by a $C_3$ Macrotricyclic Receptor, *J. Am. Chem. Soc.*, 113 (13):5111–5112 (1991); U.S.A.
Jeong, K.–S., et al., Molecular Recognition. Asymmetric Complexation of Diketopiperazines, *J. Am. Chem. Soc.*, 112:6145–6146 (1990); U.S.A.
Liu, R., et al., Enantioselective Complexation of the Alanine Dipeptide by a $C_2$ Host Molecule, *J. Org. Chem.*, 55:5184–5186 (1990); U.S.A.
Murakami, Y., et al., Capped Azaparacyclophane, *J. Chem. Soc., Chem Commun.*, 753–755 (1985); Great Britain.
Sanderson, P. E. J., et al., Enantioselective Complexation of Simple Amides by a $C_2$ Host Molecule, *J. Am. Chem. Soc.*, 111:8314–8315 (1989); U.S.A.
Wambach, L., and Vögtle, F., Tetrahydrofuran–Einschluss und Gast–Selektive Katalyse des H/D–Austauschs in Saurer Losung, *Tetrahedron Letters*, 26:1483–1486 (1985); Great Britain.

*Primary Examiner*—Mukund J. Shah
*Assistant Examiner*—Pavanaram Sripada
*Attorney, Agent, or Firm*—John P. White

[57]                ABSTRACT

The subject invention provides chiral receptor molecules having the structure:

wherein A has the structure:

and $R_1$ and $R_2$ are independently the same or different and are H, F, alkyl, aryl, etc.; X is $CH_2$ or NH; Y is C=O or $SO_2$; and n is 0 to about 3; which are useful for the purification of enantiomers of amino acid derivatives and other compounds. The subject invention also provides methods of preparing said receptor molecules.

4 Claims, 2 Drawing Sheets

A₄B₆ MACROTRICYCLIC ENANTIOSELECTIVE RECEPTORS FOR AMINO ACID DERIVATIVES, AND OTHER COMPOUNDS

This invention was made with government support under grant #GM-44525 from the National Institutes of Health and grants #CHE89-11008 and #CHE92-08245 from the National Science Foundation. Accordingly, the U.S. Government has certain rights in the invention.

This application is a continuation-in-part of U.S. Ser. No. 07/901,401, filed Jun. 19, 1992, the contents of which are hereby incorporated by reference into this application.

BACKGROUND OF THE INVENTION

This invention relates to the field of molecular recognition of small ligands. More particularly, the invention relates to compositions useful for the purification of enantiomers of amino acid derivatives and for the purification of certain compounds able to form hydrogen bonds, methods for preparing these compositions, and methods for using them.

Standard approaches to the optical resolution and purification of organic and biological molecules include crystallization, distillation, extraction, and chromatography (Eliel, *Stereochemistry of Carbon Compounds,* New York: McGraw-Hill, 1962). Each methodology is based on a physical or chemical interaction of a molecule with an element of its environment, and may involve molecular sizing, electrostatics, hydrophobicity, sterics, or polarity. The efficiency of purification increases as the differences in interaction energy for all the species present in the mixture increase. The relevant interactions for cystallization are crystal lattice forces and solvation of the molecule; for distillation, the interaction is a liquid-gas phase transition; while for extraction and chromatography, the interaction is exchange between non-miscible phases. Common to all these classic methods is the limitation that as molecular structures become increasingly similar, the energy differentials for the relevant interaction diminish to the extent that high resolution is no longer feasible. A general approach to purification necessitates an enhanced capability for transcending this natural tendency toward shrinking energy differences. The ability to purify very similar or chiral molecules is of economic and practical importance to the developing fields of biotechnology, and should greatly accelerate the development of new pharmaceuticals and bioactive and other useful compounds.

The ability to distinguish similar molecules is an important goal of research in the field of molecular recognition. Early efforts to bind molecules selectively involved naturally occurring host molecules, such as clathrates, cholic acid, and cyclodextrins (Diederich, *Angew. Chem. Int. Ed. Eng.,* 27, 362 (1988); Breslow, *Science (Washington, D.C.),* 218, 532 (1982)). The first example of a synthetic system specifically designed to undergo inclusion complexation was a cyclophane (Stetter & Roos, *Chem. Ber.,* 88, 1390 (1955)). Synthetic crown ethers and cyclic polyamines were designed to complex metal ions selectively by adjusting ring size and number of heteroatoms (Pederson, *Angew. Chem. Int. Ed. Eng.,* 16, 16 (1972)). Macrobicyclic compounds have been prepared which show selectivity for trihydrobenzenes with certain substitution patterns (Ebmeyer and Vogtle, *Angew. Chem. Int. Ed. Engl.,* 28, 79 (1989)).

The use of chiral components in constructing host compounds has led to the development of molecules which are, in principle, capable of diasteroselective complexation with chiral guests. While several systems have exhibited some diastereoselectivity, numerous attempts to produce chiral hosts have not produced any known compounds of practical utility prior to the present invention. The earliest preparations of chiral crown amino ethers were applied to cation complexation, and not to chiral discrimination by diastereoselective complexation (Wudl & Gaeta, *J. Chem. Soc., Chem. Commun.,* 107 (1972)). Chiral hosts based on biphenyl-macrocycles have shown promise (Kyba, et al., *J. Amer. Chem. Soc.,* 100, 4555 (1978)). A recent example intended to distinguish enantiomers of amino acids and arylpropionic acids however appears from binding studies not to function as a host for nonpolar molecules (Rubin, et al., *J. Org. Chem.,* 51, 3270 (1986)).

High enantioselectivity has thus largely eluded prior workers in the field. A bilaterally symmetric host containing two diiodotyrosine moieties was one of the first to exhibit a measurable difference in binding energy with mirror image guest molecules (Sanderson, et al., *J. Amer. Chem. Soc.,* 111, 8314 (1989)); free energy differences ranged from –0.15 to 0.48 kcal/mole, with binding site saturations up to 67%. More recently, a related chiral host was made with pyridyl moieties replacing benzene rings in the macrocycle, which showed free energy differences up to about 1 kcal/mole and a range of binding saturations of approximately 40–80% (Liu, et al., *J. Org. Chem.,* 55, 5184 (1990)). Chiral hosts in which the enantioselection energies exceed 1 kcal/mole have been virtually nonexistent prior to the present invention.

Progress toward a completely chemoselective or enantioselective host has been limited, proceeding roughly in parallel with growing understanding of intermolecular interactions controlling binding affinity in natural receptors like enzymes and hormone receptors. The present invention provides a composition of matter which possesses enzyme-like enantioselectivity which is sufficiently high to offer practical utility in optical organic resolution and chemical purification of compounds.

SUMMARY OF THE INVENTION

The present invention relates to a composition of matter having the structure:

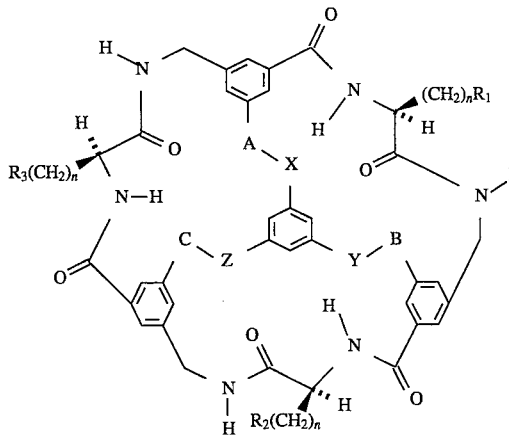

wherein each of A, B, C, X, Y, and Z is independently O, NH, N(CH$_2$)$_m$CH$_3$, N(C=O)(CH$_2$)$_m$CH$_3$, CH$_2$, S, or Se; each of R$_1$, R$_2$, and R$_3$ is independently phenyl, 4-hydroxyphenyl, pyridyl, pyrrolyl, indolyl, naphthyl, thiophenyl, (C=O)(CH$_2$)$_p$CH$_3$, NH(C=O)(CH$_2$)$_p$CH$_3$, OH, COOH, NH$_2$, or SH; and m, n, and p are integers between 0 and 5.

The invention provides a process of obtaining a purified enantiomeric isomer of a compound of interest from a mixture of isomers of such compounds which comprises contacting the mixture of isomers with the composition under conditions such that the enantiomeric isomer binds to the composition to form a complex, separating the resulting complex from the mixture, treating the complex so as to separate the enantiomeric isomer from the composition, and recovering the purified enantiomeric isomer.

The invention also provides a process of obtaining a purified organic compound of interest able to form hydrogen bonds from a mixture of organic compounds which comprises contacting the mixture with the composition under conditions such that the organic compound binds to the composition to form a complex, separating the resulting complex from the mixture, treating the complex so as to separate compound from the composition, and recovering the purified compound.

The invention further provides a process of preparing the composition which comprises: (a) reacting a chiral multifunctional reagent containing at least one protecting group with a compound having the structure:

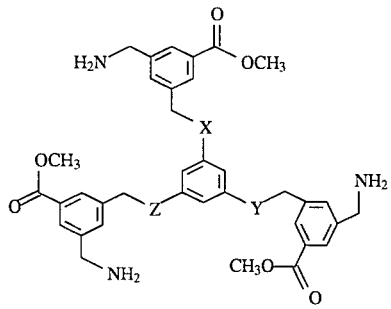

wherein each of A, B, C, X, Y, and Z is independently O, NH, $N(CH_2)_mCH_3$, $N(C=O)(CH_2)_mCH_3$, $CH_2$, S, or Se, under conditions permitting formation of a compound having the structure:

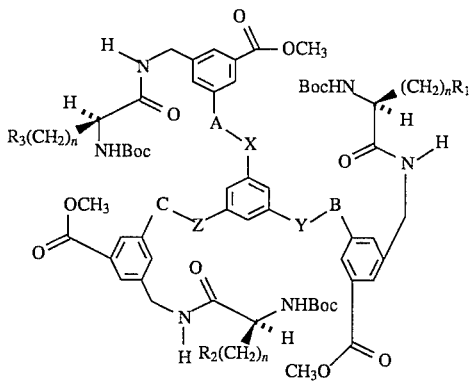

wherein each of A, B, C, X, Y, and Z is independently O, NH, $N(CH_2)_mCH_3$, $N(C=O)(CH_2)_mCH_3$, $CH_2$, S, or Se; each of $R_1$, $R_2$, and $R_3$ is independently phenyl, 4-hydroxyphenyl, pyridyl, pyrrolyl, indolyl, naphthyl, thiophenyl, $(C=O)(CH_2)pCH_3$, $NH(C=O)(CH_2)_pCH_3$, OH, COOH, $NH_2$, or SH; and m, n, and p are integers between 0 and 5;

(b) treating the compound formed in step (a) under suitable conditions so as to cleave one protecting group and form a compound having the structure:

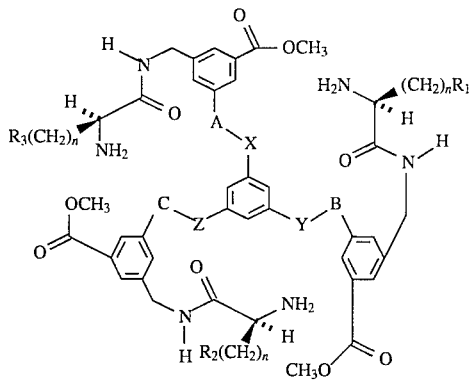

wherein each of A, B, C, X, Y, and Z is independently O, NH, $N(CH_2)_mCH_3$, $N(C=O)(CH_2)_mCH_3$, $CH_2$, S, or Se; each of $R_1$, $R_2$, and $R_3$ is independently phenyl, 4-hydroxyphenyl, pyridyl, pyrrolyl, indolyl, naphthyl, thiophenyl, $(C=O)(CH_2)_pCH_3$, $NH(C=O)(CH_2)_pCH_3$, OH, COOH, $NH_2$, or SH; and m, n, and p are integers between 0 and 5;

(c) treating the compound formed in step (b) with a condensing agent under conditions permitting multiple macrolactamization so as to thereby form the composition.

The present invention further provides a composition of matter having the structure:

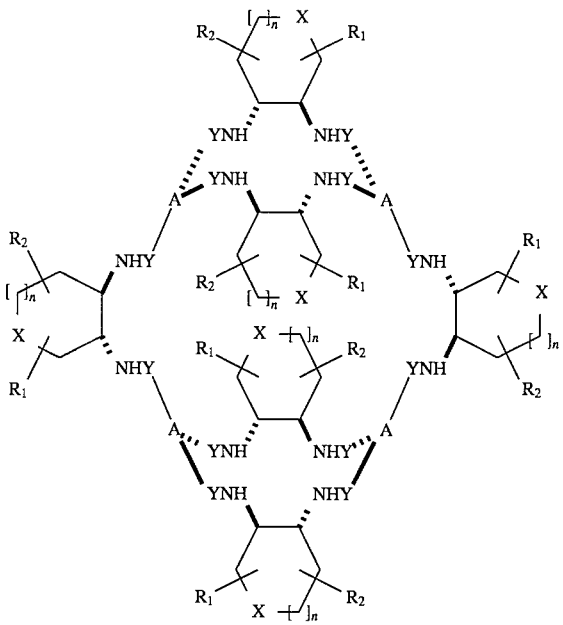

wherein A has the structure:

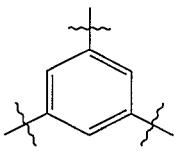

and $R_1$ and $R_2$ are independently the same or different and are H, F, a linear or branched chain alkyl, arylalkyl, alkoxyalkyl, aminoalkyl, alkylaminoalkyl, hydroxyalkyl, (cycloalkyl)alkyl, or acylalkyl group, or an aryl group, a linear or branched chain alkylaryl, pyridyl, thiophene, pyrrolyl, indolyl or naphthyl group; X is CH$_2$ or NH; Y is C=O or SO$_2$; and n is 0 to about 3.

The present invention also provides a composition of matter having the structure:

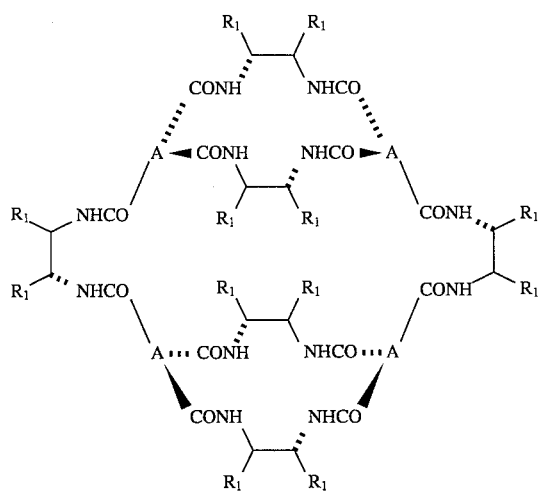

wherein A has the structure:

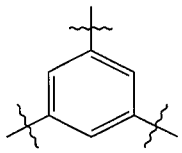

and R$_1$ is H, a linear or branched chain alkyl, arylalkyl, alkoxyalkyl, aminoalkyl, alkylaminoalkyl, hydroxyalkyl, (cycloalkyl)alkyl, or acylalkyl group, or an aryl group, a linear or branched chain alkylaryl, pyridyl, thiophene, pyrrolyl, indolyl or naphthyl group.

The present invention also provides a composition of matter having the structure:

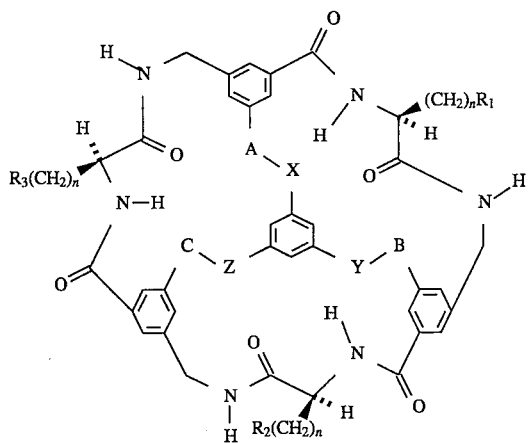

wherein R$_1$, R$_2$ and R$_3$ are C$_6$H$_4$(OCH$_2$CH=CH$_2$); A, B and C are CH$_2$; X, Y and Z are S; and n is 1.

DETAILED DESCRIPTION OF THE INVENTION

Figure 1:
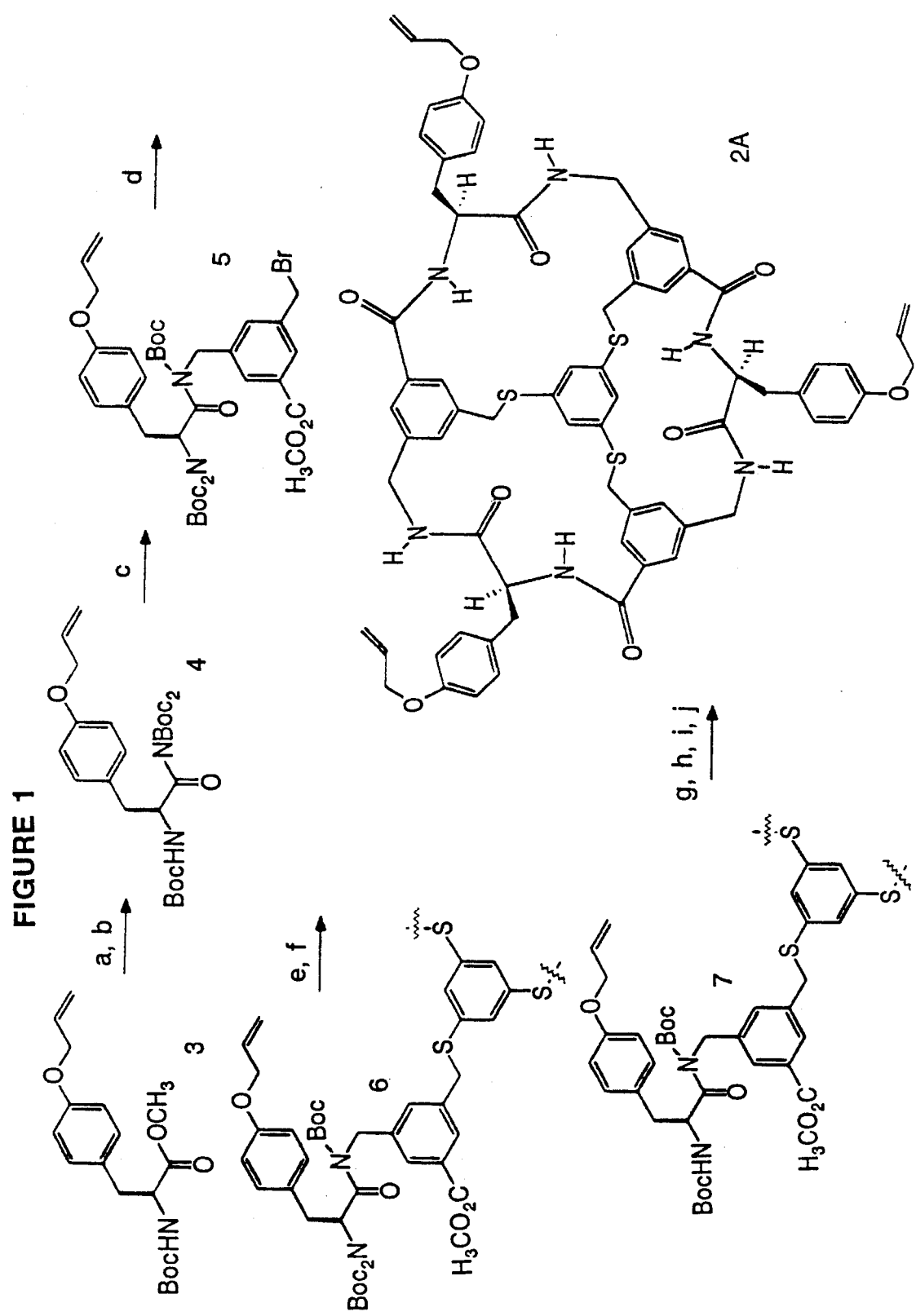
FIG. 1 shows a scheme for the practical synthesis host molecule 2: (a) Methanol/ammonia 4:1, rt, 2 days, 97%; (b) Boc$_2$O, i-Pr$_2$NEt, 4-DMAP (10 mol %), CH$_2$Cl$_2$, 1 h, 90%; (c) NaN(TMS)$_2$, THF, −78° C., 3 min; add tetra-n-butylammonium iodide and methyl 3,5-bis(bromomethyl)benzoate; warm to 10° C., 2 h, 82%; (d) benzene-1,3,5-trithiol, i-Pr$_2$NEt, THF, 8 h, 78%; (e) TFA, anisole, CH$_2$Cl$_2$, rt, 16 h, quant; (f) Boc$_2$O, i-Pr$_2$NEt, K$_2$CO$_3$, CH$_2$Cl$_2$, rt, 24 h, 86%; (g) THF, EtOH, H$_2$O, LiOH, 6 h, quant; (h) F$_5$-phenol, EDC, THF, rt, 4 h, 68%; (i) TFA, anisole, CH$_2$Cl$_2$, rt, 4 h, quant; (j) TFA salt in DMA dropwise to i-Pr$_2$NEt, THF, rt, 40 h, 78%.

The present invention provides a composition of matter having the structure:

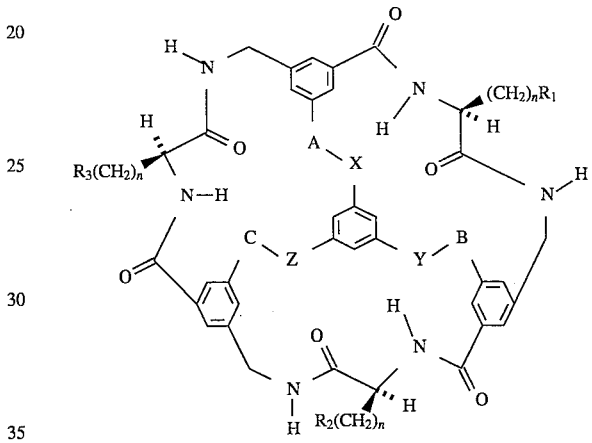

wherein each of A, B, C, X, Y, and Z is independently O, NH, N(CH$_2$)$_m$CH$_3$, N(C=O)(CH$_2$)$_m$CH$_3$, CH$_2$, S, or Se; each of R$_1$, R$_2$, and R$_3$ is independently phenyl, 4-hydroxyphenyl, pyridyl, pyrrolyl, indolyl, naphthyl, thiophenyl, (C=O)(CH$_2$)$_p$CH$_3$, NH(C=O)(CH$_2$)$_p$CH$_3$, OH, COOH, NH$_2$, or SH; and m, n, and p are integers between 0 and 5. In one embodiment of the invention, X, Y, and Z are each O; in another embodiment, they are each S. In certain other embodiments, R$_1$, R$_2$, and R$_3$ are each phenyl, or they are each 4-hydroxyphenyl. Additionally, in certain embodiments, n is desirably 1.

The invention further provides a process of obtaining a purified enantiomeric isomer of a compound of interest from a mixture of isomers of such compounds which comprises contacting the mixture of isomers with the chiral host composition defined hereinabove under conditions such that the enantiomeric isomer binds to the composition to form a complex, separating the resulting complex from the mixture, treating the complex so as to separate the enantiomeric isomer from the composition, and recovering the purified enantiomeric isomer. In one embodiment, the process is used to purify enantiomers of amino acid derivatives, of which diamides are particularly effective.

The invention also provides a process of obtaining a purified organic compound of interest from a mixture of organic compounds able to form hydrogen bonds, which comprises contacting the mixture with the chiral host composition defined hereinabove under conditions such that the organic compound binds to the composition to form a complex, separating the resulting complex from the mixture, treating the complex so as to separate the compound from the composition, and recovering the purified compound. In one embodiment, the process is used to purify derivatives of amino acids differing in side-chains. The process is particularly well suited to purify diamide derivatives of amino acids.

One application of the composition is to bind it to a solid support such that a chromatographic adsorbent results which is specific for enantiomeric isomers of compounds of interest and other organic compounds of interest which differ only in side-chain substitution. Effective use of the composition bound to a solid support is made to obtain the enantiomeric isomers of an amino acid derivative in a purified form and to obtain a purified organic compound of interest able to form hydrogen bonds from a mixture of compounds. The compound to be purified by the composition is preferably a diamide.

The invention further provides a process of preparing the composition, which comprises:

(a) reacting a chiral multifunctional reagent containing at least one protecting group with a compound having the structure:

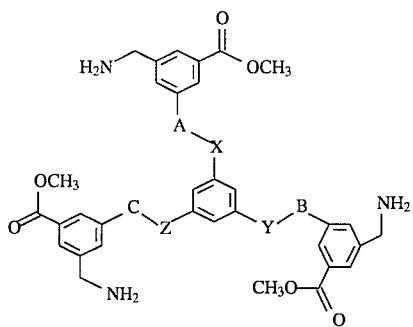

wherein each of A, B, C, X, Y, and Z is independently O, NH, $N(CH_2)_mCH_3$, $N(C=O)(CH_2)_mCH_3$, $CH_2$, S, or Se, under conditions permitting formation of a compound having the structure:

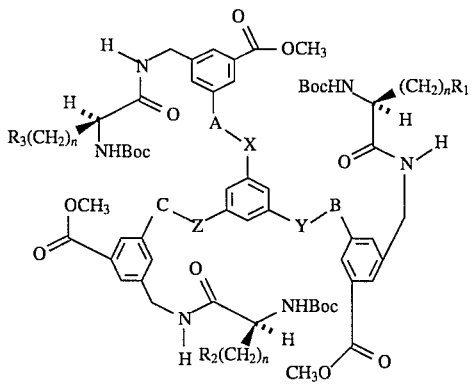

wherein each of A, B, C, X, Y, and Z is independently O, NH, $N(CH_2)_mCH_3$, $N(C=O)(CH_2)_mCH_3$, $CH_2$, S, or Se; each of $R_1$, $R_2$, and $R_3$ is independently phenyl, 4-hydroxyphenyl, pyridyl, pyrrolyl, indolyl, naphthyl, thiophenyl, $(C=O)(CH_2)_pCH_3$, $NH(C=O)(CH_2)_pCH_3$, OH, COOH, $NH_2$, or SH; and m, n, and p are integers between 0 and 5;

(b) treating the compound formed in step (a) under suitable conditions to cleave one protecting group to form a compound having the structure:

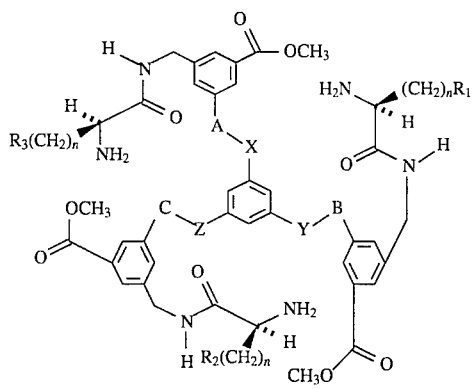

wherein each of A, B, C, X, Y, and Z is independently O, NH, $N(CH_2)_mCH_3$, $N(C=O)(CH_2)_mCH_3$, $CH_2$, S, or Se; each of $R_1$, $R_2$, and $R_3$ is independently phenyl, 4-hydroxyphenyl, pyridyl, pyrrolyl, indolyl, naphthyl, thiophenyl, $(C=O)(CH_2)_pCH_3$, $NH(C=O)(CH_2)_pCH_3$, OH, COOH, $NH_2$, or SH; and m, n, and p are integers between 0 and 5;

(c) treating the compound formed in step (b) with a condensing agent under conditions permitting multiple macrolactamization, thereby forming the desired composition.

The preparation of the composition strategically exploits its $C_3$ symmetry. The synthesis of the composition could proceed in a manner analogous to the detailed experimental examples given hereinbelow for embodiments in which X, Y, and Z are S, and $R_1$, $R_2$, $R_3$ are 4-hydroxyphenyl, except that if there is only one protecting group in the chiral multifunctional reagent of step (a), then none of the side-group protection reactions would pertain.

The coupling of step (a) above can be carried out by several alternative methods of forming amide bonds. One approach is to contact the achiral tetraaromatic triamino triester above shown with the p-nitrophenyl active ester of the chiral multifunctional reagent, made from p-nitrophenol, N-hydroxybenzotriazole, and N,N-dicyclohexylcarbodiimide. The reaction may be performed in the presence of aprotic dipolar solvents, such as N,N-dimethylformamide, tetrahydrofuran, or dimethylsulfoxide, diluted with a miscible cosolvent, such as dichloromethane, to the extent required to achieve solubility of all reactants, at temperatures from about 0° to 100° C., preferably from 0° to 30° C. The preparation of the starting material for step (a) can be obtained by trialkylation of 1,3,5-trimercaptobenzene or phloroglucinol with N-protected methyl 3-(aminomethyl)-5-(bromomethyl)benzoate, followed by cleavage of the N-protecting group. In one embodiment of the invention, the chiral multifunctional reagent containing at least one protecting group in step (a) is an amino acid containing an N-protecting group. In certain embodiments, the amino acid is L-phenylalanine or L-tyrosine. The N-protecting group is preferably chosen such that it may be removed in process step (b) by an acid, for example, trifluoroacetic acid. In general, process step (b) involves the removal of three protecting groups on the tetraaromatic intermediate. This reaction could be effected by any method corresponding to the lability of the protecting group. A large variety of protecting groups are available for the purpose, including t-butyloxycarbonyl (BOC), benzyloxycarbonyl, 2-bromobenzyloxycarbonyl, and p-toluensulfonyl. While a preferred method is to use acid-sensitive BOC groups, other effective protecting groups also removable by acid include biphenylisopropyloxycarbonyl (Bpoc) and adamantyloxycarbonyl (Adoc), Still other protecting groups may be selected such that alternative methods of removal are feasible according to the invention, including photolytic, reductive, electrochemical, and mild base conditions. This flexibility allows a wide range of chiral multifunctional reagents to be used to prepare the composition.

Prior to condensation process (c), the protecting ester group (for example, methyl) on each of the three aromatic moieties could be cleaved to give the carboxylic acid by (i) transesterification with trimethylsilylethanol, followed by (ii) fluoride-induced silane elimination. The condensing agent in step (c) could comprise a reagent generated (i) from an agent selected from a group comprising pentafluorophenol, hydroxybenzotriazole, 4-nitrophenol, 2-nitrophenol, pentachlorophenol, hydroxysuccinimide, and hydroxypiperidine and (ii) from an agent selected from a group consisting of N,N-dicyclohexyldiimide, diisopropylcarbodiimide, and carbonyldiimidazole. Other condensing methods may also serve the purpose, including Woodward's reagent K, mixed anhydrides, triphenylphosphine/2,2'-dipyridyl sulfide, ketenimines, and acyloxyphosphonium salts. In a preferred embodiment, the condensing agent is the combination of N,N-dicyclohexylcarbodiimide and pentafluorophenol. If the multifunctional chiral reagent of step (a) contains an alcohol function, the process of steps (b) and (c) could be simply adapted to generate three ester linkages after multiple macrolactonization. Other modifications in the multifunctional chiral reagent of step (a) could be readily envisioned to form such alternative linkages as thioesters, thionoesters, and phosphoramides.

The protecting groups which may be present on side-group functionalities could be cleaved by a method corresponding to their lability. In one embodiment, $R_1$, $R_2$, and $R_3$ are 4-hydroxyphenyl which should be made by coupling with the suitably protected multifunctional chiral reagent Boc-L-tyrosine (Tyr). The protecting group on the Tyr is preferably an allyl ether. The processes described provided the embodiments of the composition, wherein $R_1$, $R_2$, and $R_3$ are phenyl, in 30% overall yield for the trithia receptor and 7% yield for the trioxa receptor, respectively referred to hereinafter as 1 and 2. Preparation of the tyrosine trithia macrocycle is described in Examples 1 to 16, which serve as an enabling model illustrative for all embodiments of the composition.

The present invention also provides a composition of matter hereinafter denoted 9 having the structure:

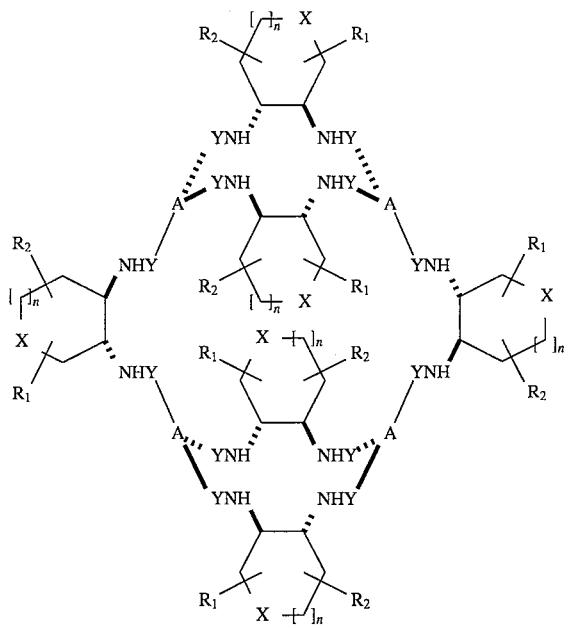

wherein A has the structure:

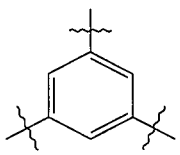

and $R_1$ and $R_2$ are independently the same or different and are H, F, a linear or branched chain alkyl, arylalkyl, alkoxyalkyl, aminoalkyl, alkylaminoalkyl, hydroxyalkyl, (cycloalkyl)alkyl, or acylalkyl group, or an aryl group, a linear or branched chain alkylaryl, pyridyl, thiophene, pyrrolyl, indolyl or naphthyl group; X is $CH_2$ or NH; Y is C=O or $SO_2$; and n is 0 to about 3. In one embodiment, the present invention provides a composition wherein X is NH.

In another embodiment, the invention provides a composition wherein X is $CH_2$, Y is C=O and n is 1. In another embodiment, the invention provides a composition wherein $R_1$ and $R_2$ are H.

The present invention also provides a composition of matter (hereinafter referred to as 10) having the structure:

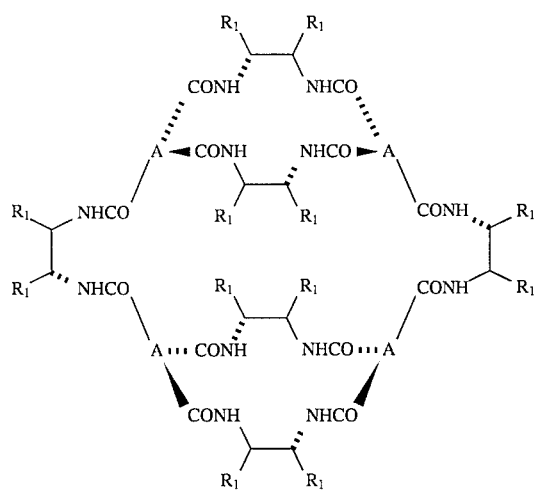

wherein A has the structure:

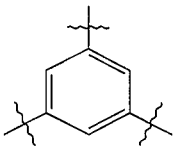

and $R_1$ is H, a linear or branched chain alkyl, arylalkyl, alkoxyalkyl, aminoalkyl, alkylaminoalkyl, hydroxyalkyl, (cycloalkyl)alkyl, or acylalkyl group, or an aryl group, a linear or branched chain alkylaryl, pyridyl, thiophene, pyrrolyl, indolyl or naphthyl group. In one embodiment, the invention provides a composition wherein $R_1$ is a phenyl group. In another embodiment, the invention provides a composition wherein $R_1$ is a benzyloxymethyl group.

The present invention further provides a composition of matter (hereinafter referred to as 2A) having the structure:

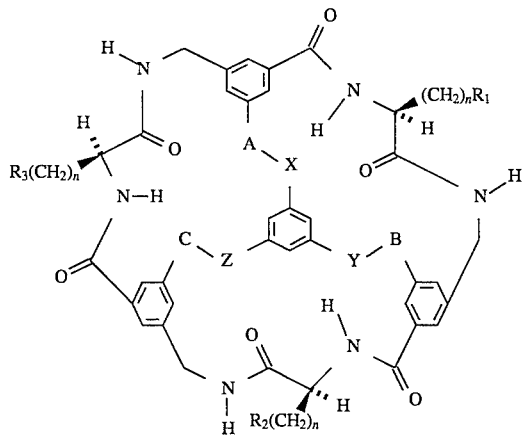

wherein $R_1$, $R_2$ and $R_3$ are $C_6H_4(OCH_2CH=CH_2)$; A, B and C are $CH_2$; X, Y and Z are S; and n is 1.

The present invention also provides a compound which comprises the compositions of matter 9, 10, or 2A, bound to a solid support.

The present invention further provides a complex which comprises the compositions 9, 10, or 2A, bound to a derivative of an amino acid. In one embodiment, the invention provides a composition wherein the derivative is an amide.

The present invention provides a process of obtaining a purified enantiomeric isomer of a compound of interest from a mixture of isomers of such compounds which comprises contacting the mixture of isomers with the compositions 9, 10, or 2A, under conditions such that the enantiomeric isomer binds to the compositon to form a complex, separating the resulting complex from the mixture, treating the complex so as to separate the enantiomeric isomer from the composition, and recovering the purified enantiomeric isomer.

The present invention further provides a process of obtaining a purified organic compound of interest from a mixture of organic compounds able to form hydrogen bonds, which comprises contacting the mixture with the compositions 9, 10, or 2A, under conditions such that the organic compound binds to the composition to form a complex, separating the resulting complex from the mixture, treating the complex so as to separate the organic compound from the composition, and recovering the purified compound. In one embodiment, the invention provides a process wherein the purified organic compound is an amino acid derivative.

The present invention also provides a process of preparing the composition having the structure:

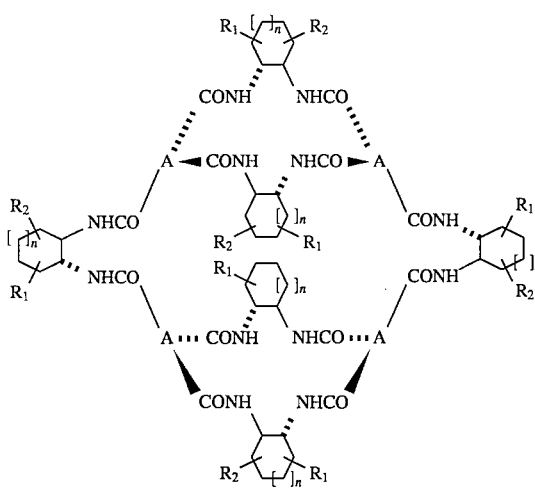

wherein A has the structure:

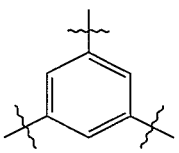

wherein $R_1$ and $R_2$ are H and n is 1 which comprises:

(a) condensing a compound having the structure:

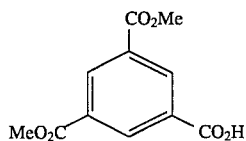

with a compound having the structure:

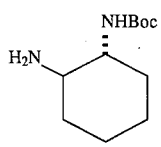

under suitable conditions to produce a compound having the structure:

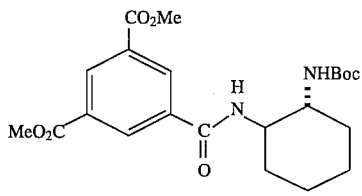

(b) hydrolyzing the compound formed by step (a) under suitable conditions to form an acid compound having the structure:

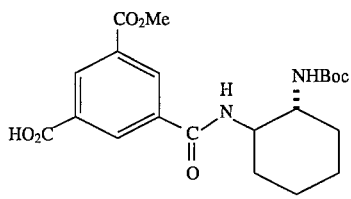

(c) treating the compound formed in step (b) under suitable conditions so as to activate the acid compound to form a compound having the structure:

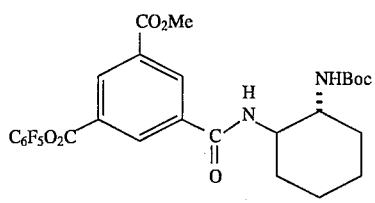

(d) reacting the compound formed in step (c) under suitable conditions with a compound having the structure:

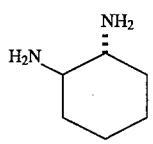

to form a compound having the structure:

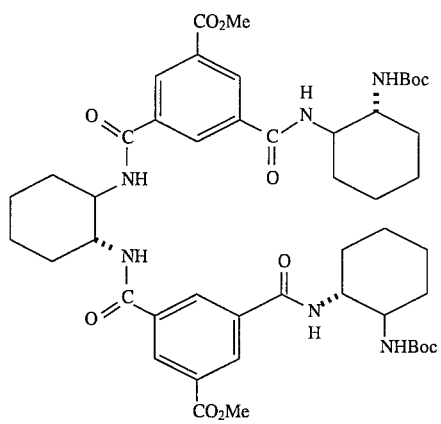

(e) saponifying the compound formed by step (d) under suitable conditions to form a diacid having the structure:

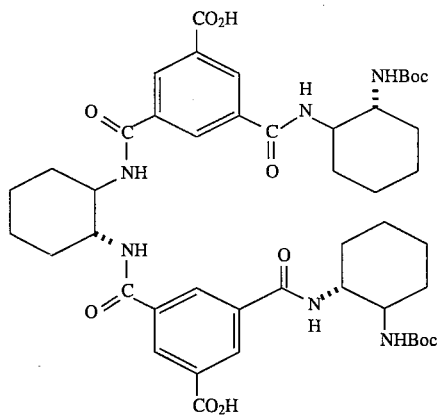

(f) activating the diacid formed in step (e) under suitable conditions to form a compound having the structure:

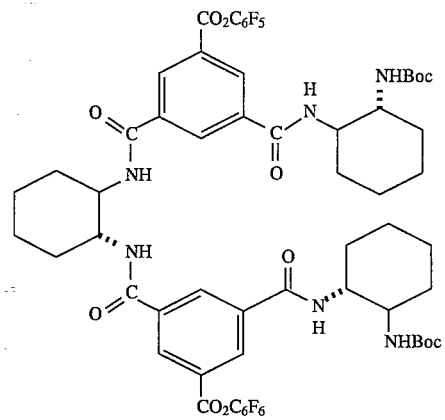

(g) deprotecting the compound formed in step (f) under suitable conditions to form a diamino diacid having the structure:

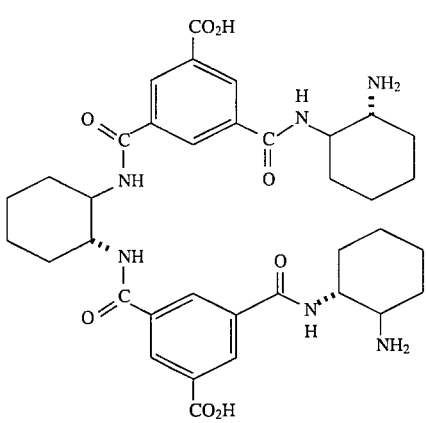

(h) dimerizing the diamino diacid formed in step (g) under suitable conditions to form the composition having the structure:

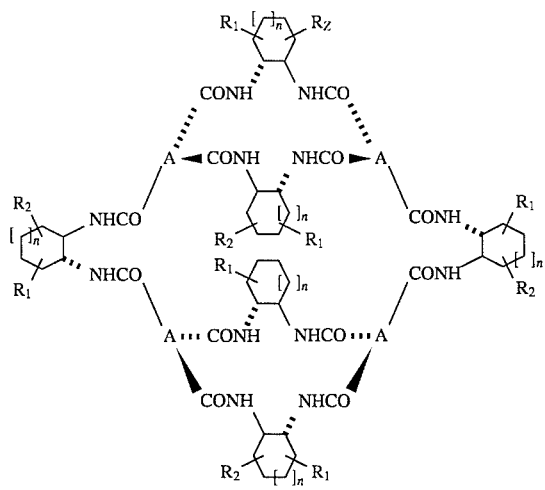

wherein A has the structure:

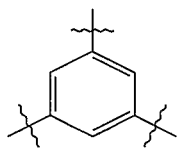

and $R_1$ and $R_2$ are H and n is 1.

In condensing step (a) it is to be understood that esters other than methyl esters may be used in an equivalent manner for the purposes of the process. Other useful esters include ethyl, propyl, phenol, and benzyl esters. The condensing agent in step (a) could comprise a reagent generated (i) from an agent selected from a group comprising pentafluorophenol, hydroxybenzotriazole, 4-nitrophenol, 2-nitrophenol, pentachlorophenol, hydroxysuccinimide, and hydroxypiperidine and (ii) from an agent selected from a group consisting of N,N-dicyclohexyldiimide, diisopropylcarbodiimide, and carbonyldiimidazole. Other condensing methods may also serve the purpose, including Woodward's reagent K, mixed anhydrides, triphenylphosphine/2,2'-dipyridyl sulfide, keteminines, and acyloxyphosphonium salts. Hydrolyzing step (b) may be performed using base or acid catalysis, though preferably base catalysis. Favorable results obtain using sodium hydroxide. Treating step (c) is effected by a wide variety of procedures, including reaction of pentafluorophenol with DCC or 1-(3-(dimethylamino)propyl)-3-ethylcarbodiimide hydrochloride (EDC). Reacting step (d) is performed in the presence of a nonnucleophilic base such as triethylamine. Good solvents for the purpose include dimethyl acetamide or dimethyl formamide. Saponifying step (e) is carried out using a base, such as sodium hydroxide. Other bases which effect the step include lithium hydroxide, potassium hydroxide, and tetramethylammonium hydroxide. Activating step (f) is effectively performed using an activating agent such as pentafluorophenol. Other agents include hydroxybenzotriazole, 4-nitrophenol, 2-nitrophenol, pentachlorophenol, hydroxysuccinimide, and hydroxypiperidine. Deprotecting step (g) is carried out preferably under mildly acidic conditions. Useful acids include trifluoroacetic, trichloroacetic acid and hydrochloric acid in dioxane solution. Scavengers such as anisole help prevent untoward alkylation reactions. Dimerizing step (h) may be effectively performed in the presence of a mild nonnucleophilic base, such as diisopropylethylamine or triethylamine in a dipolar nonaqueous solvent, such as tetrahydrofuran.

The present invention also provides a process of preparing the composition having the structure:

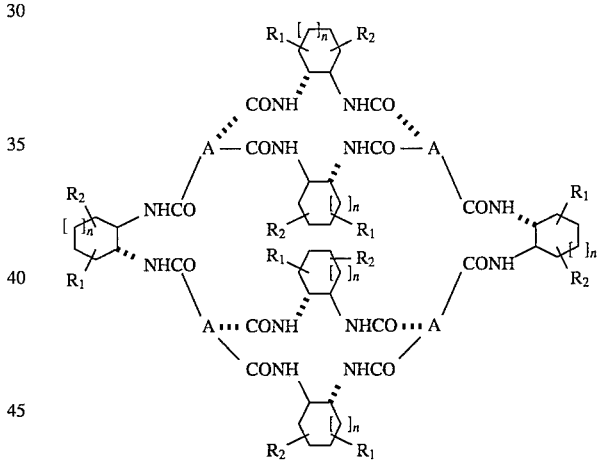

wherein A is a 1,3,5-trisubstituted phenyl moiety and $R_1$ and $R_2$ are H and n is 1 which comprises: reacting a compound having the structure:

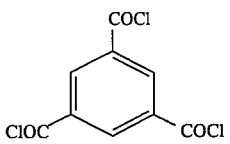

with a compound having the structure:

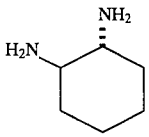

under suitable conditions to form a compound:

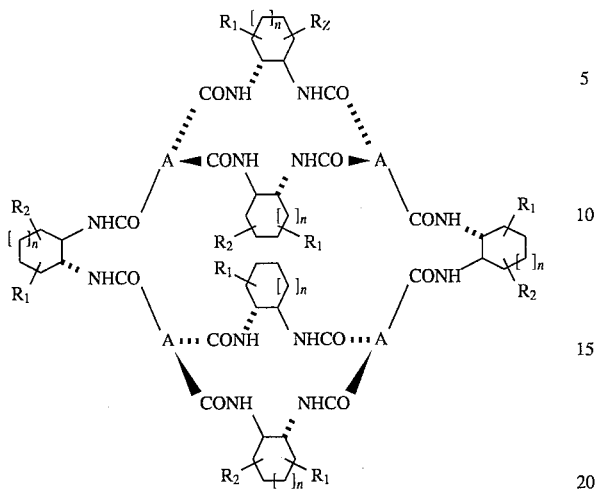

wherein A has the structure:

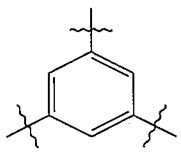

and $R_1$ and $R_2$ are H and n is 1.

The reacting step may be effectively performed as a one-pot procedure in the presence of a mild nonnucleophilic base such as diisopropylethylamine. Useful solvents include dipolar nonaqueous solvents such as dimethyl formamide and tetrahydrofuran. The reaction may be carried out over a range of temperatures from −25° C. to 60° C., but preferably at 0°–10° C.

The present invention also provides a process of preparing the composition having the structure:

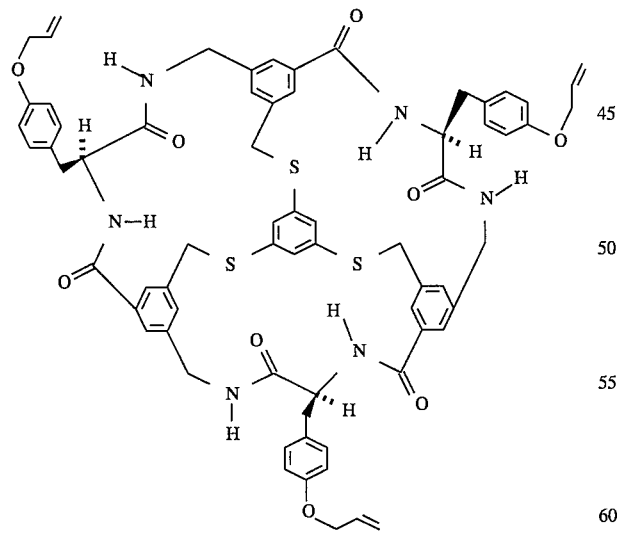

which comprises:

(a) reacting a compound having the structure:

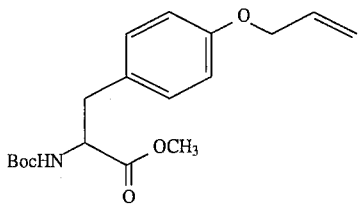

with ammonia under suitable conditions to form a compound having the structure:

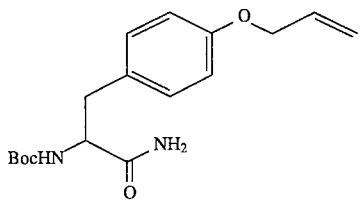

(b) reacting the compound formed by step (a) with an acylating agent under suitable conditions to form a plurally acylated compound having the structure:

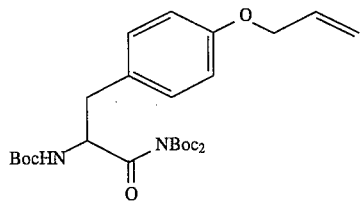

(c) reacting the plurally acylated compound formed by step (b) with a compound having the structure:

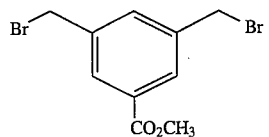

under suitable conditions to form an alkylated amide having the structure:

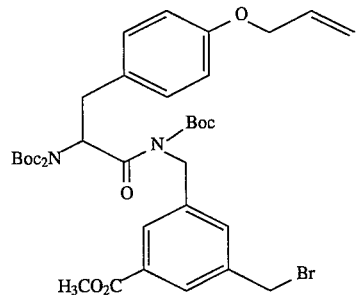

(d) reacting the alkylated amide formed by step (c) with benzene-1,3,5-trithiol under suitable conditions to form a sulfide having the structure:

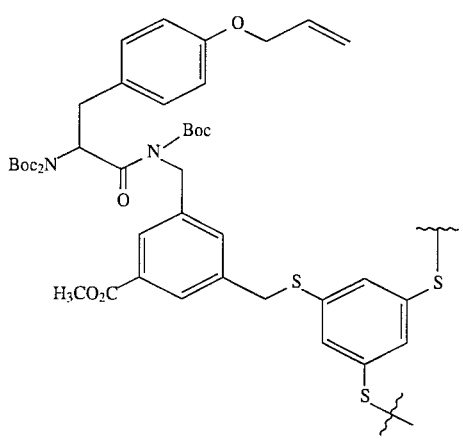

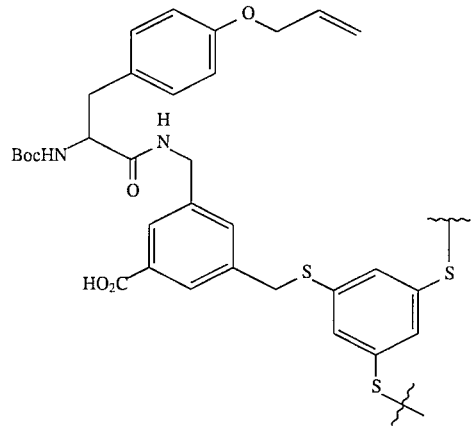

(e) deprotecting the sulfide formed by step (d) under suitable conditions to form a free amine ester having the structure:

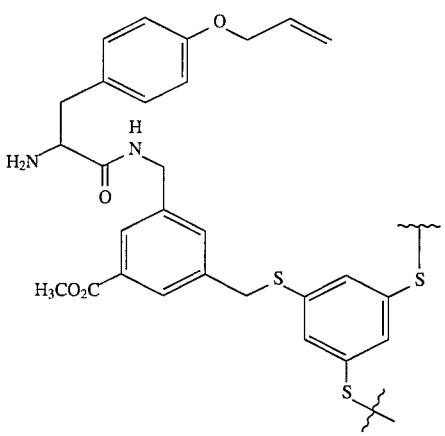

(f) re-acylating the free amine ester formed by step (e) under suitable conditions to form an acylamine ester having the structure:

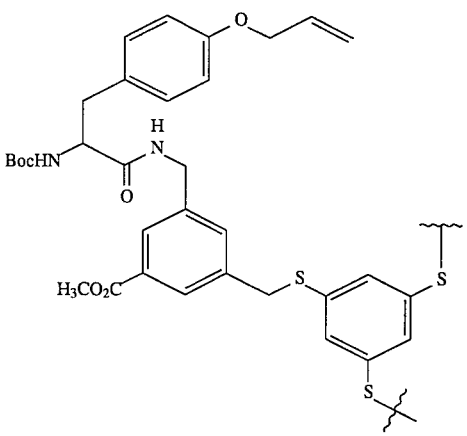

(g) saponifying the acylamine ester formed by step (f) under suitable conditions to form an acylamine acid having the structure:

(h) activating the acylamine acid formed by step (g) under suitable conditions to form an acylamine activated ester having the structure:

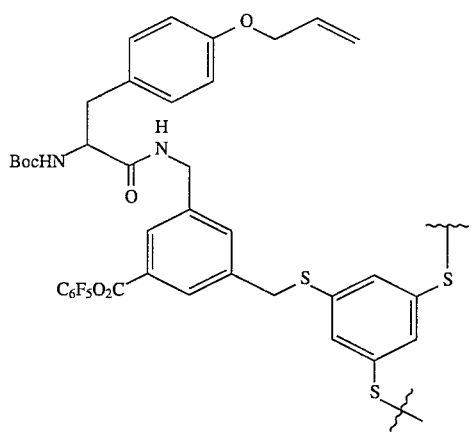

(i) de-protecting the acylamine activated ester formed by step (h) under suitable conditions to form a free amine activated ester having the structure:

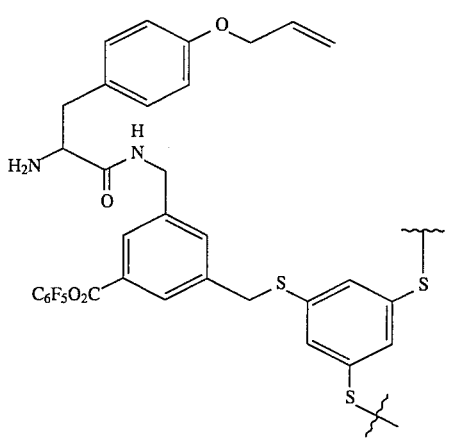

and (j) cyclizing the free amine activated ester formed by step (i) under suitable conditions to form the composition.

Reacting step (a) may be carried out in the presence of a miscible co-solvent such as methanol, and occurs in high yield when performed at ambient temperatures. Reacting step (b) may be carried out using a variety of acylating agents in the presence of nonnucleophilic base and 4-dimethylaminopyridine catalyst. Common agents include t-Boc-Cl and Amyloxycarbonyl chloride. Reacting step (c) is efficiently performed using sodium hexamethyldisilylazide in tetrahydrofuran solution. Preferred temperatures range from −80° C. to −70° C. A dry ice bath providing a temperature of −78° C. is convenient for this purpose. Reacting step (d) is readily effected in the presence of a nonnucleophilic base such as diisopropylethylamine in a dipolar nonaqueous solvent such as tetrahydrofuran. Deprotecting step (e) occurs well by using a mild acid, such as trifluoacetic acid in the presence of a scavenger such as anisole. Reacylating step (f) is carried out using a variety of acylating agents. t-Boc$_2$O is a preferred acylating agent for the purposes of the synthesis. Saponifying step (g) may be carried out using such bases as lithium hydroxide and sodium hydroxide. Lithium hydroxide is a preferred base. Activating step (h) is carried out using pentafluorophenol in the presence of various condensing agents, including DCC and EDC. De-protecting step (i) may be performed using a mild acid such as trifluoroacetic acid and a scavenger. Cyclizing step (j) is performed using a dropwise addition technique and a nonnucleophilic base such as diisopropylethylamine in a dipolar nonaqueous solvent such as dimethyl acetamide or dimethyl formamide.

Receptors 1 and 2 are capable of high binding selectivity among simple amino acid derivatives (Table I). With Boc-protected, N-methylamide acid derivatives, enantioselectivity ranges from 1.7 to 3.0 kcal/mole with the L isomer always being bound preferentially (entries 1/2, 5/6, 7/8, 9/10, 12/13).

Side-chain functionality can also be distinguished by the chiral receptors (Table I; entries 1–8 vs 9, 10 and 12, 13). The side-chain hydroxyls of serine and threonine contribute about 2 kcal/mole to association energies and effectively distinguish these amino acids from Ala, Val, and Leu. Such hydroxylated L-amino acids bind better than O-benzyl-L-serine (entry 11) by about 3 kcal/mole. Nuclear magnetic resonance data suggest that the operative mode of complexation involves close proximity of the C-terminal group of the amino acid derivatives to all four aromatic rings in the host. Entries 14–17 (Table I) suggest that other binding modes may apply to amino acid derivatives having small N-terminal functionalities such as acetyl.

The chiral host compounds may be utilized in any manner suitable for the intended purpose. For example, the host may be covalently bound to a polymer by modification of the synthetic method described above by replacing phloroglucinol or a similar starting material with one which has the additional substitution of an alkyl, aryl, or aralkyl, linker containing a reactive moiety at its terminus, comprising a halide, amine, carboxylate, alcohol, or thiol, if necessary in suitably protected form.

The resulting chiral polymer may serve as an adsorbent for use as a convenient extractive reagent, in which the polymer may be combined with a mixture of racemic amino acid derivatives or a mixture of compounds related by differing side-chain substitution in a range of polar or nonpolar solvents. After sufficient agitation at a temperature suitable for promoting binding of one component in the mixture, ranging from −90° to 180° C. preferably from 0° to 35° C., the polymeric complex is then separated by gravity or suction filtration, centrifugation, or sedimentation and decanting. The desired enantiomeric derivative or related compound may be obtained by washing the polymer with a suitable buffer, solvent, or mixture of solvents at a temperature suitable for releasing the derivative from the polymeric host. The chiral polymer may also serve as an adsorbent in a chromatographic column, in which the mixture of enantiomers or related compounds may bind with different affinities, and then be eluted after washing with a suitable buffer, solvent, or mixture of solvents. The adsorbent is preferably prepared using finer meshes (>400 U.S. mesh) of chloromethylated 0.5–2.0% divinyl-benzene cross-linked polystyrene and either aminoethyl, hydroxyethyl, or carboxyethyl derivatives of phloroglucinol or benzenetrithiol, according to the described procedure. Any polymeric resin selected from the group consisting of polyacrylamide, phenolformaldehyde polymers, polymethacrylate, carbohydrates, aluminates, and silicates may serve as the solid medium.

While not wishing to be bound by a particular theory of action, the high selectivity in the binding of various substrates to a host molecule as observed while practicing the present invention could result from high conformational homogeneity and substantial host/guest contact. Monte Carlo conformational searching using the MacroModel/AMBER force field, in which Phe is modeled by Ala, predicts that the chiral receptors have similar conformations with C3 symmetry. The Phe's are folded into turns around the periphery of a large binding cavity with dimensions (~6 Å diameter) similar to those of α-cyclodextrin. Some variability remains in the central ring Ar—X—CH$_2$—Ar' torsion angles, with little effect on the shape and nature of the binding cavity. Experimental evidence supporting the predicted structure includes NH—CH$_a$ coupling constants (J 1=8.1 Hz; J 2=8.0 Hz) and N—H infrared bands (free and hydrogen-bonded: 3434, 3321) cm$^{-1}$) in dilute CDCl$_3$ solution. The chiral host on forming a bound complex undergoes only minor conformational change, according to simulated annealing calculations. Specific contacts which may be responsible for the selective binding interactions in the complex could include three N—H/O═C hydrogen bonds, according to molecular mechanics modelling.

The chiral hosts of the present invention bind diamides of certain amino acids with high selectivity which is dependent upon the nature of the amino acid side chain (2–kcal/mol for serine vs alanine) and the identity of the N-alkyl substituent (>3 kcal/mol for methyl vs tert-butyl). These synthetic hosts are among the most enantioselective known, and bind certain derivatives of L-amino acids with selectivities as high as 3 kcal/mol. No other composition has been available to the art which achieves binding energy differentials of the magnitude herein disclosed for diastereoselective complexation of amino acid derivatives.

The following Experimental Details are set forth to aid in an understanding of the invention, and are not intended, and should not be construed, to limit in any way the invention set forth in the claims which follow thereafter.

TABLE I

ΔG's of Association (kcal/mole) of 1 and 2 with Amino Acid Derivatives

| Entry | Peptide substrate | $-\Delta G^a$ 1 | $-\Delta G^a$ 2 | Saturation$^b$ % 1 | Saturation$^b$ % 2 | $\Delta\Delta G^c$ 1 | $\Delta\Delta G^c$ 2 |
|---|---|---|---|---|---|---|---|
| 1 | N—Boc—D—Ala—NHMe | 1.7 | 2.1 | 53 | 70 | | |
| 2 | N—Boc—L—Ala—NHMe | 3.9 | 3.8 | 93 | 90 | 2.2 | 1.7 |
| 3 | N—Boc—L—Ala—NHBn | 1.4 | | 51 | | | |
| 4 | N—Boc—L—Ala—NHtBu | nc$^d$ | | | | | |
| 5 | N—Boc—D—Val—NHMe | 1.5 | 1.5 | 51 | 54 | | |
| 6 | N—Boc—L—Val—NHMe | 4.4 | 4.0 | 79 | 74 | 2.9 | 2.5 |
| 7 | N—Boc—D—Leu—NHMe | 1.5 | 1.6 | 64 | 60 | | |
| 8 | N—Boc—L—Leu—NHMe | 4.1 | 3.8 | 88 | 78 | 2.6 | 2.2 |
| 9 | N—Boc—D—Ser—NHMe | 3.8 | 4.4 | 86 | 94 | | |
| 10 | N—Boc—L—Ser—NHMe | >6.1 | >6.2 | 95 | 96 | >2.3 | >1.8 |
| 11 | N—Boc—L—Ser(OBn)—NHMe | 3.1 | | 83 | | | |
| 12 | N—Boc—D—Thr—NHMe | 3.2 | 3.6 | 84 | 90 | | |
| 13 | N—Boc—L—Thr—NHMe | >6.2 | 1 g$^e$ | >95 | | >3.0 | |
| 14 | N—Ac—D—Ala—NHMe | 2.7 | | 90 | | | |
| 15 | N—Ac—L—Ala—NHMe | 3.9 | | 94 | | 1.2 | |
| 16 | N—Ac—D—Ala—NHtBu | 2.0 | | 59 | | | |
| 17 | N—Ac—L—Ala—NHtBu | 3.0 | | 85 | | 1.0 | |

$^a$Measured by NMR titration at 25 C. with 1 or 2 at 0.5 mM concentration in CDCl$_3$.
$^b$Extent of extrapolated saturation at end of titration.
$^c$Enantioselectivity, ΔG(D) − ΔG(L).
$^d$No complexation detected.
$^e$Too large to measure accurately.

Experimental Details

EXAMPLE 1

Preparation of methyl-3,5-dimethyl-benzoate:

A solution of 3,5-dimethyl benzoic acid (25 g, 0.17 mol) in methanol (250 ml) was treated with sulfuric acid (1 ml, cat. amount) and heated to reflux. After 10 hours, the solution was cooled to room temperature, concentrated to approximately 1/2 volume and poured into 200 ml of crushed ice. The mixture was extracted twice with 200 ml portions of diethyl ether. The organic phase was extracted with saturated aqueous sodium carbonate, dried over magnesium sulfate, and concentrated under reduced pressure. The resulting solid was recrystallized from hexanes to yield the product (24.5 g, 90% yield) as volatile white plates. mp=32°–35° C. (lit. mp=35°–36° C.)

EXAMPLE 2

Preparation of methyl-3,5-bis(bromomethyl)-benzoate:

A solution of methyl-3,5-dimethyl-benzoate (16.8 g, 0.10 mol) in carbon tetrachloride (150 ml) was treated with N-bromosuccinimide (35.6 g, 0.20 mmol), and benzoyl peroxide (500 mg, cat. amount), and heated to reflux. After 3 hours, the mixture was cooled to room temperature and filtered through a sintered glass funnel. The filtrate was concentrated under reduced pressure and recrystallized from diethyl ether/hexanes (1:1) to yield the product (18.0 g, 55% yield) as a granular white solid. mp 64°–70° C. (lit. mp 65°–69° C.); TLC (20% ethyl acetate/hexanes): R$_f$=0.65 (UV active, CAM stain)

EXAMPLE 3

Preparation of methyl-3-bromomethyl-5-bis(Boc)aminomethyl-benzoate:

A mixture of sodium hydride (3.6 g, 90 mmol) and N,N-dimethylformamide (150 ml) was cooled to 0° C. and treated with solid di-tert-butyliminodicarboxylate (17.4 g, 76.0 mmol) with vigorous stirring. The mixture was stirred at 0° C. for 15 minutes, the ice bath was removed and a solution of methyl-3,5-bis(bromomethyl)-benzoate (23.6 g, 73.2 mmol) in N,N-dimethylformamide was added dropwise over 30 minutes. After 12 hours the mixture was poured into 100 ml 1/4 saturated aqueous ammonium chloride and extracted with the three 100 ml portion of hexanes. The organic layer was dried over magnesium sulfate, concentrated under reduced pressure and chromatographed using a gradient of 10–20% ethyl acetate/hexanes to yield the product (22.0 g, 66% yield). TLC (20% ethyl acetate/hexanes): R$_f$=0.55 (UV active, CAM stain)

EXAMPLE 4

Preparation of benzene-1,3,5-tris)methyl-3'-thiomethyl-5'-bis(Boc)aminomethyl-benzoate];

A solution of benzene-1,3,5-trithiol (900 mg, 5.16 mmol) in tetrahydrofuran (60 ml) was treated with N,N-diisopropylethylamine (3.1 ml, 17.67 mmol) with vigorous stirring. The mixture was allowed to stir until all solids had dissolved and was treated with solution of methyl-3-bromomethyl-5-bis(Boc)aminomethyl-benzoate (8.1 g, 17.67 mmol) in tetrahydrofuran. After 24 hours the mixture was poured into 100 ml saturated aqueous ammonium chloride and extracted with three 100 ml portions of diethyl ether. The organic phase was dried over magnesium sulfate, concentrated under reduced pressure, and the resulting oil was chromatographed using a gradient of 20–40% ethyl acetate/hexanes to yield the product (5.10 g, 76% yield) as a colorless oil. TLC (40% ethyl acetate/hexanes): R$_f$=0.65 (UV active, Cl$_2$/TDM stain)

EXAMPLE 5

Preparation of benzene-1,3,5-tris[methyl-3'-thiomethyl-5'-aminomethyl-benzoate hydrochloride salt]:

A solution of benzene-1,2,3,5-tris[methyl-3'-thiomethyl-5'-bis(Boc)aminomethyl-benzoate hydrochloride](4.8 g, 3.67 mmol) in absolute methanol (25 ml) was treated with 25 ml "10% methanolic HCl" (a mixture of 2.5 ml acetyl chloride and 22.5 ml absolute methanol) and allowed to stir at room temperature for 3 hours. All volatiles were removed under reduced pressure and the resulting white powder was dried under high vacuum. The product (3.00 g, quant. yield) was used without additional purification.

EXAMPLE 6

Preparation of N-α-Boc-L-tyrosine methyl ester: A solution of L-tyrosine methyl ester hydrochloride (10.0 g, 43.2 mmol) in N,N-dimethylformamide (100 ml) was cooled to 0° C. and treated with solid di-tert-butyl dicarbonate (13.0 g, 65 mmol) and triethylamine (6.6 ml, 47.5 mmol). After one hour the ice bath was remove and the solution was allowed to warm to room temperature. After 4 hours the solution was poured into 200 ml ethyl acetate, extracted with 100 ml 1.0M aqueous hydrochloric acid, 200 ml saturated aqueous sodium bicarbonate, 200 ml saturated aqueous sodium chloride, dried over magnesium sulfate, and concentrated under reduced pressure. The crude product (12.56 g, 98% yield) was used without additional purification.

EXAMPLE 7

Preparation of N-α-BOC-L-tyrosine-O-allyl ether methyl ester:

A solution of N-α-BOC-L-tyrosine methyl ester (12.5 g, 42.3 mmol) in N,N-dimethylformamide (100 ml) was treated with allyl bromide (4.5 ml, 51.8 mmol), tetra-n-butylammonium iodide (1.5 g, 4.3 mmol) and potassium carbonate (12 g, 86.4 mmol) and allowed to stir overnight. After 14 hours the mixture was poured into 200 ml ethyl acetate and extracted with 100 ml 1.0M aqueous citric acid, 100 ml saturated aqueous sodium bicarbonate, saturated aqueous sodium chloride, dried over magnesium sulfate and concentrated under reduced pressure. The resulting oil was chromatographed using a gradient of 20–40% ethyl acetate/hexanes to yield the product (14.0 g, 99% yield) a colorless oil. TLC (40% ethyl acetate/hexanes): $R_f$=0.40 (UV active, $Cl_2$/TDM stain)

EXAMPLE 8

Preparation of N-α-BOC-L-tyrosine-O-allyl ether:

A solution of N-α-BOC-L-tyrosine-O-allyl ether methyl ester (14.0 g, 41.7 mmol) in a mixture of tetrahydrofuran (100 ml) and water (10 ml) was treated with lithium hydroxide (10.0 g, 260 mmol) and allowed to stir at room temperature. After 6 hours all of the starting material had been consumed, as determined by thin layer chromatography, and the reaction mixture was diluted with 200 ml ethyl acetate and acidified to pH 2 with 1.0M aqueous potassium hydrogen sulfate. The organic phase was dried over magnesium sulfate and concentrated under reduced pressure to yield the product (13.4 g, quant. yield). The product was used without additional purification.

EXAMPLE 9

Preparation of N-α-BOC-L-tyrosine-O-allyl ether-p-nitrophenyl ester:

A solution of N-α-BOC-L-tyrosine-O-allyl ether (13.4 g, 41.7 mmol) in chloroform (100 ml) was cooled to 0° C. and was treated with p-nitrophenol (17 g, 128 mmol), N-hydroxybenzotriazole (3.0 g, 21.3 mmol) and N,N'-dicyclohexylcarbodiimide (10.5 g, 51.2 mmol). The mixture was allowed to stir overnight at room temperature. After 15 hours the solution was filtered to remove N,N'-dicyclohexylurea, concentrated under reduced pressure and chromatographed using 100% chloroform to yield the product (13.7 g, 74% yield) as a yellow oil which solidified upon standing. TLC (100% chloroform): $R_f$=0.30 (UV active, ninhydrin stain)

EXAMPLE 10

Preparation of benzene-1,3,5-tris[methyl-3'-thiomethyl-5'-aminomethyl-(N-α-BOC-L-tyrosine-amide-O-allyl-ether) benzoate]:

A solution of benzene-1,3,5-tris[methyl-3'-thiomethyl-5'-aminomethyl-benzoate hydrochloride salt] (2.33 g, 2.86 mmol) in N,N-dimethylformamide (30 ml) was treated with N,N-diisopropylethylamine (1.9 ml, 10.87 mmol) with vigorous stirring until all solids had dissolved. The solution was cooled to 0° C. and treated with solid N-α-BOC-L-tyrosine-O-allyl-ether-p-nitrophenyl ester (2(0 (4.3 g, 9.72 mmol). After one hour the ice bath was removed and the mixture was mixed with silica gel (13 g) and all volatiles were removed under reduced pressure. The preabsorbed reaction mixture was placed directly onto a chromatography column containing silica gel equilibrated with 40% ethyl acetate/hexanes. The column was eluted with 40% ethyl acetate/hexanes to remove unreacted p-nitrophenyl ester and most of the p-nitrophenol. The product was then eluted with 10% methanol/chloroform to yield a fine yellow powder slightly contaminated with p-nitrophenol. The mixture was redissolved in methylene chloride and extracted with two 200 ml portions of 0.5M aqueous sodium hydroxide. The organic phase was dried over magnesium sulfate and concentrated under reduced pressure to yield to product (4.41 g, 96% yield) as a pale yellow powder. TLC (8% acetone/methylene chloride): $R_f$=0.45 (UV active, $Cl_2$/TDM stain)

EXAMPLE 11

Preparation of benzene-1,3,5-tris[2'-(trimethyl)silylethyl-3'-thiomethyl-5'-aminomethyl-(N-α-Boc-L-tyrosine-amide-O-allyl-ether)-benzoate]:

A suspension of benzene-1,3,5-tris[methyl-3'-thiomethyl-5'-aminomethyl-(N-α-BOC-L-tyrosine-amide-O-allyl-ether)benzoate] (4.3 g, 2.66 mmol) in 2-(-trimethyl)silylethanol (10 ml, 70 mmol) and toluene (10 ml) was thoroughly purged with argon and treated with titanium ethoxide (0.050 ml, catalytic amount) and heated to reflux. After 6 hours the mixture was cooled to room temperature, filtered through a pad of Celite (diatomaceous earth) and concentrated under reduced pressure. The resulting oil was chromatographed using a gradient of 100% methylene chloride-5% methanol/methylene chloride to yield the product (4.2 g, 84% yield) as a pale yellow powder. TLC (8% acetone/methylene chloride): $R_f$=0.85 (UV active, $Cl_2$/TDM stain).

EXAMPLE 12

Preparation of benzene-1,3,5-tris[3'-thiomethyl-5'-aminomethyl-(N-α-BOC-L-tyrosine-amide-O-allyl-ether)-benzoic acid]:

A solution of benzene-1.3.5-tris[2'-(trimethyl)silylethyl-3'-thiomethyl-5'-aminomethyl-)N-α-BOC-L-tyrosine-amide-O-allyl-ether)-benzoate] (4.2 g, 2.24 mmol) in tetrahydrofuran (75 ml) was treated with tetra-n-butylammonium fluoride (1.0M solution in tetrahydrofuran) (10.08 ml, 10.08 mmol). After 4 hours the solution was diluted with 100 ml ethyl acetate and acidified to pH 2 with 1.0M aqueous potassium hydrogen sulfate. The organic layer was dried over magnesium sulfate and concentrated under reduced pressure to yield the product (3.50 g, quant. yield). The product was used without additional purification.

TLC (10% methanol/chloroform): $R_f$=0.15 (UV active, $Cl_2$/ TDM stain).

EXAMPLE 13

Preparation of benzene-1,3,5-tris[pentafluorophenyl-3'-thiomethyl-5'-aminomethyl-(N-α-BOC-L-tyrosine-amide-O-allyl-ether)-benzoate]:

A solution of benzene-1,3,5-tris[3'-thiomethyl-5'-aminomethyl-(N-α-BOC-L-tyrosine-amide-O-allyl-ether)-benzoic acid] (3.50 g, 2,24 mmol) in tetrahydrofuran (50 ml) was treated with pentafluorophenol (3.7 g, 20.16 mmol), and was allowed to stir at room temperature. After 3 hours the reaction mixture was concentrated under reduced pressure and the resulting oil was chromatographed using a gradient of 100% methylene chloride-10% acetone/methylene chloride to yield the product (2.60 g, 56% yield) as a white powder.

TLC (5% acetone/methylene chloride): $R_f$=0.45 (UV active, CAM stain)

EXAMPLE 14

Preparation of benzene-1,3,5-tris[{pentafluorophenyl-3'-thiomethyl-5'-aminomethyl-(L-tyrosine-amide-O-allyl-ether)-benzoate}-trifluoroacetate salt]:

A solution of benzene-1,3,5-tris[pentafluorophenyl-3'-thiomethyl-5'-aminomethyl-(N-α-BOC-L-tyrosine-amide-O-allyl-ether)-benzoate] (2.5 g, 1.21 mmol) in methylene chloride (100 ml) was treated with anisole (10.0 ml, 93.0 mmol) and trifluoroacetic acid (50.0 ml). After 3 hours the mixture was concentrate under reduced pressure, resuspended in toluene and concentrated again. Finally, the product was triturated three times in diethyl ether to yield the product (1.90 g, quant. yield) as a white powder. The product was used without additional purification.

EXAMPLE 15

Preparation of L-tyrosine macrocycle tris-allyl ether: benzoate}-trifluoroacetate salt] (1.47 g, 1.21 mmol) in N,N-dimethylacetamide (25 ml) was added via syringe pump (33 hours) to a stirring solution of N,N-diisopropylethylamine (30.0 ml, 180 mmol) in tetrahydrofuran (500 ml). Twelve hours after the addition had been completed, the reaction mixture was diluted with an equal volume of ethyl acetate, extracted with two 200 ml portions of 5% aqueous hydrochloric acid, two 200 ml portions of saturated aqueous sodium bicarbonate, and 100 ml saturated aqueous sodium chloride. The organic phase was dried over magnesium sulfate, concentrated under reduced pressure and chromatographed using a gradient of 100% chloroform—5% methanol/chloroform to yield the product (892 mg, 65% yield) as a pale yellow powder. TLC (25% acetone methylene chloride): $R_f$=0.45 (UV active, CAM stain).

EXAMPLE 16

Preparation of the L-tyrosine macrocycle 1:

A solution of the L-tyrosine macrocycle tris-allyl ether (50 mg, 0.041 mmol) in tetrahydrofuran (15 ml) was treated with 5,5-dimethyl-cyclohexan-1,3-dione (100 mg, 0.71 mmol) and tetrakis-(triphenylphosphine)palladium (10.0 mg, cat. amount) and allowed to stir at room temperature. After 4 hours the solution was diluted with 50 ml ethyl acetate and extracted with three 20 ml portions of saturated aqueous sodium bicarbonate and 20 ml saturated aqueous sodium chloride. The organic phase was dried over magnesium sulfate and concentrated under pressure. The resulting solid was chromatographed using 10% methanol/chloroform to yield the product (1; 40.0 mg, 89% yield) as a pale yellow powder. TLC (10% methanol/chloroform): $R_f$=0.20 (UV active, CAM stain).

EXAMPLE 17

Preparation of a receptor bound to a solid support:

A solid phase peptide reaction vessel was charged with Merrifield resin (chloromethylated polystyrene crosslinked with 2% divinylbenzene; 100 mg, 0.100 meq), the macrocyclic tris-phenol made according to Example 16 (110.0 mg, 0.100 mmol), potassium carbonate (14 mg, 0.100 mmol), and N,N-dimethylformamide (2 ml). The mixture was placed on a rotary agitator for four days. The reaction mixture was washed successively with 5×5 ml portions of methylene chloride, methanol, deionized water, methanol, and methylene chloride. The resulting solid was dried under high vacuum and weighed to dermine the amount of alkylation. The coupled resin weighed 116.3 mg (approximately 15% based on chloromethyl groups). The organic washes were diluted with 100 ml ethyl acetate and extracted with 50 ml portions of 1M aqueous potassium hydrogen sulfate, saturated aqueous sodium bicarbonate, and saturated aqueous sodium chloride. The organic phase was dried over magnesium sulfate, concentrated under reduced pressure, and chromatographed using 10% methanol/chloroform to recover unreacted tris-phenol (40.1 mg). The infrared spectrum shows type I, II, and III amide bands (1650, 1510, and 1230 $cm^{-1}$).

EXAMPLE 18

Method of resolution of N-α-Boc-DL-valine methylamide: The resin-bound tyrosine receptor (50 mg) prepared in Example 17 was placed in a solid-phase peptide synthesis reaction vessel (a cylinderical glass container with a ground glass joint (standard taper 14/20) on top, a coarse glass frit, and a stopcock at the bottom; treated with dichlorodimethylsilane to reduce adhesion to the glass surface) was pre-swelled by washing 5 times with 50 ml portions of chloroform and forcing excess solvent out with a stream of argon. A solution of 10 mM N-α-BOC-DL-valine methylamide (57.6 mg) was dissolved in perdeuterobenzene, and incubated with the resin-bound host for five minutes. The resin was washed with acetone (5 times 50 ml). The collected washings were concentrated under reduced pressure to afford 14.5 mg of resolved N-α-BOC-valine methylamide. The extent of enantiomeric enrichment was determined as follows. The BOC group was removed by treatment with a large excess of anhydrous methanolic HCl. On neutralization with triethylamine, the resulting amine was reacted with N-α-BOC-L-alanine p-nitrophenyl ester to give N-α-BOC-L-alanylvaline methylamide (19.0 mg, 97.2%) after chromatography. NMR integration and comparison with authentic DL diastereomeric compounds revealed an 85:15 mixture of diastereomers, i.e., 70% enantiomeric enrichment. The resin could be regenerated by washing five times with 50 ml portions of methanol, dried under a stream of argon, and re-swelled with chloroform.

EXAMPLE 19

Synthesis of an O-allyl tyrosyl $C_3$-Symmetric receptor: N-Boc-O-Allyl-L-tyrosine amide 3.

Di-tert-butyl dicarbonate (13.0 g, 59.6 mmol) was added to a solution of L-tyrosine methyl ester hydrochloride (10.0 g, 43.2 mmol) and i-$Pr_2NEt$ (6.6 mL, 38.0 mmol) in DMF (100 mL). The reaction mixture was poured into 1M aq KHSO$_4$ after 8 h and extracted with ethyl acetate (3×). The combined extracts were washed with aq NaHCO$_3$ and brine. Drying and evaporation afforded a yellow oil which was dissolved in DMF (100 mL). Potassium carbonate (12.0 g, 86 mmol), allyl bromide (4.5 mL, 51.8 mmol), and n-Bu$_4$-NI (1.5 g, 4.3 mmol) were added. The reaction mixture was stirred for 16 h, poured into 1M aq KHSO$_4$, and extracted with ethyl acetate (3×). The combined organic layers were washed with aq NaHCO$_3$ and brine. Drying and solvent removal afforded N-Boc-O-allyl-L-tyrosine methyl ester as a yellow oil.

Ammonia (20 mL) was condensed into a solution of N-Boc-O-allyl-L-tyrosine methyl ester in CH$_3$OH (60 mL) at −78 °C. in a high pressure glass reaction vessel. The vessel was sealed and slowly warmed to rt. After 2 days, the vessel was cooled to −78 °C. and opened. Argon was bubbled through the solution while it was allowed to warm slowly to rt. After 1 h, the solution was transferred to a round-bottom flask and all volatiles were removed. The light brown solid residue was washed with hexane/ethyl acetate (2:1) to yield the N-Boc-O-allyl-L-tyrosine amide 3 (13.0 g, 94%) as a white solid: mp 145° C.; R$_f$ 0.28 (diethyl ether); $^1$H NMR (CDCl$_3$) δ1.40 (9H, s), 2.97 (1H, dd, J=7.2, 13.6 Hz), 3.05 (1H, dd, J=6.4, 13.6 Hz), 4.30 (1H, m), 4.51 (d, J=5.2 Hz), 5.06 (1H, m), 5.29 (1H, dd, J=1.4, 10.8 Hz), 5.38 (1H, dd, J=1.2, 19.2 Hz), 5.40 (1H, bs), 5.78 (1H, bs), 6.04 (1H, m), 6.86 (2H, d, J=8.4 Hz), 7.13 (2H, d, J=8.4 Hz); $^{13}$C NMR (CDCl$_3$) δ27.9, 37.3, 55.2, 68.5, 77.2, 114.6, 117.3, 128.4, 130.0, 132.9, 148.8, 157.3, 173.7; IR (KBr) 3677, 3390, 3195, 1678, 1661, 1515, 1248, 1168 cm$^{-1}$; HRMS calcd for C$_{17}$H$_{24}$N$_2$O$_4$ 320.1736; found 320.1741.

N-Boc-O-Allyl-L-tyrosine N,N-di-Boc-amide 4.

To a solution of 3 (3.0 g, 9.38 mmol) in CH$_2$Cl$_2$ at rt was added i-Pr$_2$-NEt (6.52 mL, 37.5 mmol), DMAP (192 mg, 1.56 mmol), and di-tert-butyl dicarbonate (5.12 g, 23.5 mmol). After 2 h the reaction mixture was washed with 1M aq KHSO$_4$ and 1M aq NaHCO$_3$. Drying, concentration, filtration through a pad (10 g) of silica gel with 30% ether in pentane and evaporation afforded crude 4 (4.39 g, 90%) as a pale yellow oil. Trituration with hexane gave 4 as a white amorphous solid: mp 87° C.; R$_f$ 0.55 (50% ether/hexane); $^1$H NMR (CDCl$_3$) δ1.36 (9H, s), 1.53 (18H, s), 2.76 (1H, dd, J=6.8, 14.0 Hz), 3.13 (1H, dd, J=4.8, 14.0 Hz), 4.51 (d, J=5.2 Hz), 5.05 (1H, d, J=9.6 Hz), 5.26 (1H, dd, J=1.6, 10.0 Hz), 5.41 (1H, dd, J=1.6, 18.0 Hz), 5.57 (1H, dd, J=4.8, 6.8 Hz), 6.05 (1H, m), 6.84 (2H, d, J=8.4 Hz), 7.12 (2H, d, J=8.4 Hz); $^{13}$C NMR (CDCl$_3$) δ27.6, 28.3, 38.3, 54.8, 68.8, 79.6, 85.2, 114.6, 117.5, 128.1, 130.7, 133.4, 149.2, 155.0, 157.8, 174.7; IR (KBr) 2979, 2361, 1788, 1728, 1609, 1511, 1458, 1368, 1316, 1224, 1144, 1011 cm$^{-1}$; HRMS (M+1) calcd for C$_{27}$H$_{43}$N$_2$O$_8$ 521.2863, found 521.2854. Anal. Calcd for C$_{26}$H$_{42}$N$_2$O$_8$: C,62.05; H,8.10; N,5.36. Found: C,62.29; H,7.70; N,5.38.

Boc-Amidomethyl methyl (bromomethyl)benzoate 5.

NaN(TMS)$_2$(1M THF; 4.75 mL, 4.75 mmol) was added dropwise to a solution of 4 (2.50 g, 4.81 mmol) in THF (40 mL) at −78 °C. Methyl 3,5-bis(bromomethyl)benzoate (1.86 g, 5.77 mmol) and n-Bu$_4$NI (431 mg, 1.17 mmol) were added after 5 min, and the reaction mixture was warmed to 10°–15° C. After 45 min the reaction mixture was diluted with ether (40 mL) and washed with aq NH$_4$Cl. The aqueous phase was extracted with ether (2×) and the extracts were washed with brine. Drying, concentration, and flash chromatography (10–20% ethyl acetate/hexane) afforded 5 (2.96 g, 82%) as a white foam; R$_f$ 0.45 (50% ether/hexane); $^1$H NMR (CDCl$_3$) δ1.33 (9H, s), 1.42 (18H, s), 3.09 (1H, dd, J=8.4, 14.0 Hz), 3.44 (1H, dd, J=6.4, 14.0 Hz), 3.89 (3H, s), 4.45 (2H, s), 4.51 (d, J=5.2 Hz), 4.56 (1H, J=15.2 Hz), 4.95 (1H, dd, J=15.2 Hz), 5.29 (1H, d, J=10.8 Hz), 5.41 (1H, d, J=17.6 Hz), 5.72 (1H, dd, J=6.0, 8.4 Hz), 6.05 (1H, m), 6.81 (2H, d, J=8.4 Hz), 7.18 (2H, d, J=8.4 Hz), 7.50 (1H, s), 7.90 (1H, s), 7.92 (1H, s); $^{13}$C NMR (d$_6$-DMSO) δ27.2, 27.3, 33.2, 35.0, 48.0, 52.2, 61.5, 68.1, 82.0, 83.1, 114.3, 117.1, 120.9, 128.0, 128.7, 130.1, 130.5, 133.8, 133.8, 139.0, 139,3. 151.9, 151.9, 156.8, 165.6, 173.6; IR (film) 3286, 2979, 2933, 1787, 1752, 1710, 1611, 1511, 1481, 1458, 1368, 1302, 1238, 1142, 1027, 999, 923 cm$^{-1}$; HRMS (M+1) calcd for C$_{37}$H$_{50}$O$_{10}$N$_2$Br 763.2637, found 763.2755.

Nona-Boc Trisulfide 6.

Compound 5 (2.0 g, 2.63 mmol) was added to a suspension of benzene-1,3,5-trithiol$^6$ (140 mg, 0.80 mmol) and i-Pr$_2$NEt (610 μL, 35.1 mmol) in THF (20 mL) at rt. The reaction mixture was quenched with aq NH$_4$Cl after 6 h and extracted with ether (2×). After a brine wash and concentration, flash chromatography (5–3:1:1 pentane:benzene:diethyl ether) gave 6 (1.38 g, 78%) as a solid white foam: mp 80° C.; R$_f$ 0.35 (33% hexane/diethyl ether); $^1$H NMR (CDCl$_3$) δ1.31 (27H, s), 1.40 (54H, s), 3.13 (3H, dd, J=8.4, 13.2 Hz), 3.44 (3H, dd, J=6.0, 13.2 Hz), 3.86 (9H, s), 4.08 (6H, s), 4.50 (6H, d, J=5.2 Hz), 4.54 (3H, d, J=15.2), 4.98 (3H, J=15.2 Hz), 5.27 (3H, J=9.6 Hz), 5.40 (3H, d, J=15.2 Hz), 5.71 (3H, dd, J=6.0, 8.4 Hz), 6.03 (3H, m), 6.82 (6H, d, J=8.4 Hz), 7.02 (3H, s), 7.19 (6H, d, J=8.4 Hz), 7.51 (3H, s), 7.86 (6H, s); $^{13}$C NMR (d$_6$-DMSO) δ27.2, 27.3, 35.0, 35.7, 48.0, 52.0, 61.4, 81.9, 83.0, 114.3, 117.1, 120.9, 124.2, 127.1, 128.5, 129.8, 130.5, 132.6, 133.8, 137.6, 138.0, 138.9, 151.3, 151.8, 156.8, 165.6, 173.6; IR (film) 3420, 2979, 1791, 1733, 1653, 1636, 1609, 1558, 1511, 1474, 1457, 1436, 1368, 1314, 1219, 1145, 1011, 960, 926, 850, 772, cm$^{-1}$. Anal. Calcd for C$_{117}$H$_{150}$N$_6$O$_{30}$S$_3$: C,63.40; H,6.82; N,3.79. Found: C,62.87; H,6.80; N,3.68.

Tri-Boc Trisulfide 7.

Trifluoroacetic acid (75 mL) and anisole (19 mL) were added via syringe to a solution of 6 (11.4 g, 5.15 mmol) in CH$_2$Cl$_2$ (150 mL) at rt. After 18 h, concentration gave a light pink residue which was triturated with ether to yield a white powder (low resolution mass spectrophotometric data; m/z= 1316). That material was dissolved in DMF (80 mL) containing K$_2$CO$_3$ (3.78 g, 31 mmol), i-Pr$_2$NEt (5.4 mL, 31 mmol), and di-tert-butyl dicarbonate (5.61 g, 25.75 mmol). After 17 h, the reaction mixture was poured into ethyl acetate (1000 mL) and washed with 1M aq KHSO$_4$, NaHCO$_3$, and brine. Drying, concentration, and trituration with ether afforded 7 (7.07 g, 85%) as a white powder: mp 138° C.; R$_f$ 0.39 (10% acetone/CH$_2$Cl$_2$); $^1$H NMR (d$_6$-DMSO) δ1.29 (27H, s), 2.67 (3H, dd, J=10.4, 14.0 Hz), 2.86 (3H, dd, J=4.4, 14.0 Hz), 3.76 (9H, s), 4.10 (3H, m), 4.27 (12H, m), 4.45 (6H, d, J=5.2 Hz), 5.20 (3H, d, J=10.4 Hz), 5.33 (3H, J=17.6 Hz), 6.04 (3H, m), 6.77 (6H, d, J=8.4 Hz), 7.10 (3H, s), 7.11 (6H, d, J=8.4 Hz), 7.51 (3H, s), 7.73 (3H, s), 7.81 (3H, s), 8.50 (3H, m); $^{13}$C NMR (d$_6$-DMSO) δ27.2, 30.8, 35.8, 36.6, 41.7, 52.1, 56.2, 68.0, 78.0, 114.2, 117.2, 123.7, 127.0, 128.1, 129.8, 130.1, 132.6, 133.8, 137.7, 140.6, 155.3, 156.6, 162.3, 165.9, 172.0,; IR (KBr) 3310, 2926, 1720, 1511, 1437, 1367, 1310, 1242, 1167, 1024 cm$^{-1}$. Anal. Calcd for C$_{87}$H102N$_6$O$_{18}$S$_3$: C,64.66; H,6.36; N,5.20. Found: C,64.07; H,6.50; N,5.02.

Pentafluorophenyl Ester of 7.

A solution of 1M aq LiOH (15 mL, 15 mmol) was added to 7 (500 mg, 0.309 mmol) in THF/EtOH/H$_2$O (6:3:2, 100 mL). The reaction mixture was poured into 1M aq KHSO$_4$ after 8 h and extracted with ethyl acetate (3×). After the extracts were washed with brine and dried, solvent removal afforded the crude acid as a light brown powder which was washed with ether.

Pentafluorophenol (600 mg, 3.26 mmol) and 1-(3-(dimethylamino)propyl)-3-ethylcarbodiimide hydrochloride (320 mg, 1.69 mmol) were added to a stirred solution of the crude acid (470 mg) in THF (7.0 mL). After 4 h of stirring, concentration gave a brown residue from which the tris(pentafluorophneyl ester) (435 mg, 68%) was isolated by flash chromatography (0–10% acetone/$CH_2Cl_2$) as an amorphous white solid: mp 158° C.; $R_f$ 0.24 (5% acetone/$CH_2Cl_2$); $^1$H NMR ($CDCl_3$) δ1.35 (27H, s), 2.98 (6H, d, J=7.2 Hz), 4.02 (6H, s), 4.35 (6H, d, J=4.4 Hz), 4.44 (6H, ddd, J=1.6, 1.8, 5.6 Hz), 5.25 (3H, dd, J=1.6, 10.4 Hz), 5.36 (3H, dd, J=1.6, 17.2 Hz), 5.99 (3H, dddd, J=1.6, 1.8, 10.4, 17.2 Hz), 6.76 (6H, d, J=8.4 Hz), 6.98 (3H, s), 7.05 (6H, d, J=8.4 Hz), 7.34 (3H, s), 7.90 (3H, s), 7.99 (3H, s); $^{13}$C NMR ($CDCl_3$) δ29.5, 32.3, 39.0, 39.3, 44.1, 57.5, 70.1, 81.7, 116.1, 119.0, 128.9, 129.9, 130.1, 131.4, 131.6, 134.5, 135.7, 138.7, 140.0, 140.9, 141.0, 157.0, 158.9, 163.3, 173.5; IR (KBr) 3371, 2979, 1686, 1615, 1517, 1444, 1368, 1224, 1166 $cm^{-1}$. Anal. Calcd for $C_{102}H_{93}F_{15}O_{18}S_3$: C, 59.13; H,4.52; N,4.06. Found: C,58.53; H,4.52; N,4.06.

Tyrosine Macrocycle 2A.

Anisole (12 mL) and trifluoroacetic acid (60 mL) were added via syringe to a stirring solution of the above tris(pentafluorophenyl ester) (3.16 g, 1.52 mmol) in $CH_2$—$Cl_2$ (125 mL). After 6 h, the reaction mixture was concentrated. The resulting pink oil was triturated with ether to yield the tris-TFA amine salt as a white powder (3.20 g).

A solution of the above tris-TFA amine salt (1.50 g, 0.710 mmol) in N,N-dimethylacetamide (25 mL) was added dropwise over 36 h to a rapidly stirred solution of i-$Pr_2NEt$ (30 mL, 172 mmol) in THF (1200 mL) at rt. After the solution was stirred for an additional 12 h, 800 mL of THF was removed and the remaining solution was diluted with ethyl acetate (400 mL). The solution was then washed with 0.5M aq HCl (2×), aq $NaHCO_3$ (2×), and brine. Drying, concentration, and flash chromatography (10–50% acetone in $CH_2Cl_2$) afforded 2A as an amorphous white solid (680 mg, 78%): mp 200° C.; $R_f$ 0.38 (20% acetone/$CH_2Cl_2$); $^1$H NMR ($CDCl_3$) δ3.09 (3H, dd, J=7.2, 14.0 Hz), 3.24 (3H, dd, J=7.2, 14.0 Hz), 3.78 (3H, d, J=15.2 Hz), 4.03 (3H, dd, J=4.2, 14.2 Hz), 4.11 (3H, d, J=15.2 Hz), 4.38 (3H, dd, J=6.8, 14.2 Hz), 4.53 (6H, d, J=5.2 Hz), 4.80 (3H, dd, J=7.2, 15.6 Hz), 5.28 (3H, dd, J=1.2, 9.6 Hz), 5.41 (3H, dd, J=1.2, 17.2 Hz), 6.04 (3H, m), 6.65 (3H, d, J=8.0 Hz), 6.68 (3H, s), 6.83 (3H, bs), 6.92 (6H, d, J=8.4 Hz), 7.08 (3H, s), 7.21 (6H, d, J=8.4 Hz), 7.44 (3H, s), 7.55 (3H, s); $^{13}$C NMR ($CDCl_3$) δ32.3, 35.8, 37.6, 45.0, 56.1, 70.2, 116.3, 119.1, 127.3, 129.7, 130.3, 131.5, 131.6, 131.8, 134.2, 134.5, 134.7, 137.9, 140.0, 141.0, 158.9, 168.6, 172.4; IR (KBr) 3310, 2926, 1654, 1510, 1457, 1242, 1178, 1113, 1019, 926, 824 $cm^{-1}$; HRMS calcd for $C_{69}H_{66}N_6O_9S_3$ 1219.4130, found 1219.4093.

EXAMPLE 20

Determination of Optical Purity of 5.

$K_2CO_3$ (20 mg, 0.145 mmol) was added to a stirred solution of 3 (100 mg, 0.131 mmol) in $CH_3OH$ (2 mL). After 30 min, the reaction mixture was filtered, diluted with ether (10 mL), and washed with aq $NH_4Cl$ and brine. Concentration followed by flash chromatography (20% diethyl ether/pentane) afforded N-Boc-O-allyltyrosine methyl ester (40.0 mg, 92%).

The above methyl ester was dissolved in $CH_3OH$ (5.0 mL) and acetyl chloride (1.0 mL, 13.5 mmol) was carefully added by pipette. After 3 h, all volatiles were removed and the resulting white solid was taken up in diethyl ether which was washed with 0.5M aq LiOH and brine. Drying and solvent removal afforded O-allyl-tyrosine methyl ester as a waxy solid (26.8 mg, 95%).

O-Allyltyrosine methyl ester (20 mg, 0.084 mmol) was added to a stirred solution of (S)-(−)-methoxy(trifluoromethyl)phenyl-acetic acid (28.0 mg, 0.120 mmol) and DCC (40 mg, 0.20 mmol) in $CH_2Cl_2$ (0.50 mL). After 3 h the reaction mixture was diluted with $CH_2Cl_2$ (10.0 mL), filtered, and washed with 0.5M aq NaOH. Drying and solvent removal afforded the crude (S)-(−)-methoxy-(trifluoromethyl)phenyl-acetamide as a waxy oil containing DCC and N,N-dicyclohexylurea: $R_f$ 0.55 (50% ether/hexane); $^1$H NMR ($CDCl_3$) δ3.05 (1H, dd, J=6.4, 14.4 Hz), 3.13 (1H, dd, J=5.4, 14.4 Hz), 3.24 (3H, s), 3.74 (3H, s), 4.52 (2H, d, J=5.2 Hz), 4.87 (1H, ddd, J=5.4, 6.0, 6.4 Hz), 5.29 (1H, d, J=10.4 Hz), 5.41 (1H, d, J=17.6 Hz), 6.06 (1H, m), 6.83 (2H, d, J=8.4 Hz), 7.05 (2H, d, J=8.4 Hz), 7.28 (1H, d, J=6.0 Hz), 7.39 (3H, m), 7.52 (2H, m); $^{13}$C NMR ($CDCl_3$) δ28.9, 37.0, 52.5, 53.4, 53.7, 55.0, 69.0, 77.9, 115.2, 117.8, 127.8, 128.1, 128.7, 129.8, 130.4, 133.4, 158.0, 166.2, 171.9,; IR (film) 3411, 3140, 2953, 2851, 1745, 1696, 1511, 1244, 1233, 1224, 1178 $cm^{-1}$; HRMS (M+1) calcd for $C_{23}H_{25}F_3NO_5$ 452.1685, found 452.1685.

O-Allyltyrosine methyl ester (20 mg, 0.084 mmol) was added to a stirring solution of (RS)-(±)-methoxy(trifluoromethyl)-phenylacetic acid (28.0 mg, 0.120 mmol) and DCC as described in the preceding paragraph to yield an authentic mixture of diastereomeric MTPA amides: $R_f$ 0.55 and 0.57 (50% ether/hexane); $^1$HNMR ($CDCl_3$) δ2.95–3.15 (2 H, m), 3.24/3.46 (3H, s), 3.74/3.76 (3H, s), 4.50 (2H, m), 4.80–5.0 (1H, m), 5.26 (1H, d, J=10.4 Hz), 5.38 (1H, d, J=17.4 Hz), 6.03 (1H, m), 6.71/6.83 (2H, d, J=8.4 Hz), 6.77/7.05 (2H, d, J=8.4 Hz), 7.28 (1H, m), 7.39 (3H, m), 7.50 (2H, m); $^{13}$C NMR ($CDCl_3$) δ28.9, 36.62, 37.0, 52.2, 52.5, 53.4, 53.7, 54.6, 69.0, 77.9, 114.6, 114.7, 117.4, 117.5, 127.1, 127.7, 128.2, 128.3, 129.1, 129.3, 129.9, 130.0, 133.0, 158.0, 166.2, 171.9; IR (film) 3411, 3140, 2953, 2851, 1745, 1696, 1511, 1244, 1233, 1224, 1178 $cm^{-1}$; HRMS (M+1) calcd for $C_{23}H_{25}F_3NO_5$ 452.1685, found 452.1695.

EXAMPLE 21

One-step synthesis of 9.

To an ice cold solution of (−)-(1R,2R)-diaminocyclohexane (24 mg, 0.211 mmol) and $iPrNEt_2$ (0.11 mL, 0.417 mmol) in THF (100 mL) and dimethylacetamide (10 mL) was added 1,3,5-benzenetricarbonyl trichloride (36 mg, 0.139 mmol) as a single portion with stirring. After 2 hours at 0° C., the mixture was allowed to warm to room temperature and stirred for an additional 12 hours. All volatiles were then removed at reduced pressure and the residue was purified by flash chromatography on silica gel using methylene chloride:methanol=97:3 to give, as the most mobile compound, an amorphous white solid (9; 5.8 mg, 13%) $^1$H NMR ($CDCl_3$) δ8.58 (s, 1H), 8.47 (s, 1H), 8.19 (s, 1H), 7.80 (d, 1H, J=6.84 Hz), 7.51 (m, 1H), 7.11 (m, 1H), 4.31 (m, 1H), 4.09 (m, 1H), 3.71 (m, 1H), 2.33 (m, 1H), 2.17 (m, 1H), 2.08 (m, 1H), 1.94 (m, 1H), 1.70–1.03 (m, 8H); $^{13}$C NMR ($CDCl_3$) δ169.2, 166.4, 165,3, 135.1, 134.8, 133.8, 130.2, 129.6, 128.1, 57.5, 54.7, 52.4, 32.6, 31.7, 31.2, 25.0, 24.7, 24.1; IR (neat) 3336, 2937, 1644, 1537, 1322 $cm^{-1}$; MS (FAB)m/z 1309 (M+). HRMS (FAB) calcd for $C_{72}H_{85}O_{12}N_{12}$ 1309.6410, found 1309.6311.

Results and Discussion

I

Unlike most synthetic host molecules (Notable exceptions: Petti, M. A.; Shepodd, T. J.; Barrans, R. E.; Dougherty, D. A. *J. Am. Chem. Soc.* 1988 110, 6825. Mock, W. L.; Shih, N.-Y. *J. Am. Chem. Soc.* 1989, 111, 2697. Sherman, J. C.; Cram, D. J. *J. Am. Chem. Soc.* 1989, 111, 4527. Jeong, K.-S.; Muehldorf, A. V.; Rebek, J. *J. Am. Chem, Soc.* 1990, 112, 6144. Hong, J.-I.; Namgoong, S. K.; Bernardi, A.; Still, W. C. *J. Am. Chem. Soc.* 1991, 113, 5111. Webb, T. H.; Suh, H.; Wilcox, C. S. *J. Am. Chem. Soc.* 1991, 113, 5111. Webb, T. H.; Suh, H.; Wilcox, C. S. *J. Am. Chem. Soc.* 1991, 113, 8554. Tanner, M. E.; Knobler, C. B.; Cram, D. J. *J. Org. Chem.* 1992, 57, 40) biological receptors are conformationally well defined and large enough to almost fully encapsulate the substrates which they often bind with exquisite selectivity. Constructing analogous synthetic receptors is challenging because such structures seem to require complex atomic networks to form large binding sites and position binding functionality.

A practical synthesis of a highly enantioselective, $C_3$-symmetric host molecule 2A has been developed. The basic strategy is a significant improvement over the relatively lengthy previous synthesis and involves direct addition of a Boc-tyrosine amide anion derivative 4 to methyl 3,5-bis(bromomethyl)-benzoate to give an advanced intermediate 5. The final step, a triple macrolactamization, closes three 19-membered rings simultaneously to produce the bridged macrotricyclic receptor in 70–80% yield.

The $C_3$-symmetric receptor 1A (Hong, J.-L. I.; Namgoong, S. K.; Bernardi, A.; Still, W. C. *J. Am. Chem. Soc.* 1991, 113, 5111) described hereinabove is one of the most enantioselective synthetic receptors yet reported and binds N-Boc-N'-methylamide derivatives of simple amino acids with enantioselectivity ranging from 2 to 3 kcal/mol (90–99% ee) (Other enantioselective hosts for neutral molecules: Canceill, J.; Lacombe, L.; Collet, A.; *J. Am. Chem. Soc.* 1985, 107, 6993. Pirkle, W. H.; Pochapsky, T. C. *J. Am. Chemo Soc.* 1987, 109, 5957. Sanderson, P. E. J.; Kilburn, J. D.; Still, W. C. *J. Am. Chem. Soc.* 1989, 111, 8314. Castro, P. P.; Georgiadis, T. M.; Diederich, F. *J. Org. Chem,* 1989, 54, 5384. Liu, R.; Sanderson, P. E. J.; Still, W. C. *J. Org. Chem.* 1990, 55, 5184. Jeong, K.-S.; Muehldorf, A. V.; Rebek, J. *J. Am. Chem. Soc.* 1980, 112, 6144. Webb, T. H.; Suh, H.; Wilcox, C. S. *J. Am. Chem. Soc.* 1991, 113, 8554). Such highly enantioselective receptors could have practical applications as resolving agents. A practical synthesis is provided hereinabove of O-allyl tyrosyl receptor 2A, a derivative of 1A which could be covalently bound to a solid support.

For a derivative of 1A which could be bound to a solid support, the O-allyl derivative 2A is appropriate. Such otherwise stable ethers can be deprotected (Kunz, H.; Unverzagt, C. *Angew. Chem., Int. Ed. Engl.* 1984, 23, 436) with transition metals to free phenols or attached (Tambute, A.; Begos, A.; Lienne, M.; Macaudiere, P.; Caude, M.; Rosset, R.; *New J. Chem.* 1989, 13, 625) directly to a support using free radical chemistry. The present synthesis avoids the problematic di-tert-butyl iminodicarboxylate anion coupling and addition of nitrogen and amino acid in separate steps. Instead, a more convergent route is provided in which an N-anionic amino acid fragment would be added to bis(bromomethyl)benzoate in a single step. Use of a Boc-stabilized amide ion made from N-Boc-O-allyltyrosine amide is summarized in FIG. 1, and proved more reactive to acylation than was the primary amide. Thus, the major product with 1 equiv of Boc$_2$O/DMAP, the tri-Boc material could be isolated in 95% yield.

As shown in FIG. 1, the desired Boc-stabilized amide anion could nevertheless be obtained and the planned coupling achieved. Thus starting with commercially available O-allyl-N-Boc-tyrosine methyl ester 3, $NH_3$ was used to prepare the corresponding primary amide which then formed the tri-Boc derivative 4.

On treatment of 4 with sodium hexamethyldisilylazide in THF at −78° C., a rapid deprotonation and Boc-migration occurred, leading to the Boc-stabilized amide anion shown below. While this anion was stable enough to be alkylated with benzylic bromides at low temperatures, warming it to 15° C. caused elimination of tert-butoxide leading to 8. For preparation of 2A, 1.2 equiv of 3,5-bis-(bromomethyl)benzoate were used with Bu$_4$NI catalysis and obtained 5 in 82% yield.

Although the alkylation proceeded smoothly, 5 might be acidic enough to have racemized under the basic conditions of the alkylation. To test for such racemization, a sample of 5 was treated with $K_2CO_3$ in methanol and then HCl in methanol. The first treatment converted (Flynn, D. A.; Zelle, R. E.; Grieco, P. A. *J. Org. Chem.* 1983, 48, 2824) the C-terminal Boc-amide to methyl ester while the second removed the two N-terminal Boc groups, yielding O-allyl-tyrosine methyl ester. This material was then coupled using DCC to (S)-α-methoxy-α-(trifluoromethyl)phenylacetic acid (Mosher's acid) to provide the corresponding amide. $^1H$ and $^{13}C$ NMR comparison of this material with corresponding amides from authentic D- and L-O-allyltyrosine methyl ester showed that very little (<5%) racemization had occurred. Under the conditions of an $^1H$ NMR experiment, as little as 2% of the epimerized D-tyrosine derivative could have been detected.

The benzylic bromide 5 was then used to triply alkylate sym-trimercaptobenzene (Bellavita, V. *Chim. Ital.* 1932, 62, 655) using Hunig's base (i-Pr$_2$NEt) providing $C_3$-symmetric 6 in 78% yield. The remainder of the synthesis involved a triple macrolactamization via an activated benzoic acid ester. However, the Boc-substituted amide was quite labile toward acid and base, and conversion of the methyl ester to acid was difficult in its presence. Furthermore, the problematic Boc could not be removed from the C-terminal amide without simultaneously deprotecting the tyrosyl amine. An effective solution to the problem was to remove all Boc protecting groups with TFA and then restore Boc protection of the free amines with Boc$_2$O to obtain 7 in 86% yield over both steps.

The three methyl esters of 7 were hydrolyzed using aqueous lithium hydroxide and then the resulting acids were esterfied to pentafluorophenol using 1-(3-(dimethylamino)propyl)-3-ethylcarbodiimide in THF. Flash chromatography (Still, W. C.; Kahn, M.; Mitra, A. *J. Org. Chem.,* 1978, 43, 2923) provided the activated tris(pentafluorophenyl ester) in 68% yield. After removing the remaining Boc protecting groups using trifluoroacetic acid, the crude trifluoroacetate salt in N,N-dimethylacetamide was added via syringe pump to a large volume of dry THF containing excess Hunig's base. The addition was carried out at room temperature over 36 h using a syringe pump and the final concentration of reactant was ~0.5 mM. This triple macrolactamization was suitable for reactions of this type and provided 2A in 78% yield after silica gel chromatography.

II

A practical synthesis of the $C_3$-symmetric receptor 2A is provided which proceeds in an overall yield of 27% and requires no high resolution chromatographic separations. Solution-phase binding experiments in CDCl$_3$ showed that 2A bound N-Boc-N'-methylamides of amino acids with the same high enantioselectivities as found with 1A. Receptor 2A is useful in solid-phase resolution of protected amino acids.

Also described herein is an example of a large synthetic receptor which has only minimal structural complexity, but has binding selectivities approaching those of biological receptors. This receptor 9 is an $A_4B_6$ cyclooligomer of trimesic acid (A) and (R,R)-diaminocyclohexane (B). It binds amino acid residues in peptide chains with very high selectivities for chirality (up to 99+% ee) and side-chain identity (up to 3+ kcal/mol).

In designing 9, minimal receptor flexibility was achieved by using fragments having few opportunities for conformational isomerism and by joining them with planar amide bonds. Because one of the fragments (A) has three joining points, the neutral, nonpolymeric condensation products of A and B are bridged polycyclics. Among the ways in which A and B can be combined, structure 9 is appealing because of its well-defined binding cavity and appropriately positioned hydrogen-bonding groups.

9 was made by first preparing an amide-linked Boc-B-A-B-A-B-Boc oligomer having the two internal carboxylates activated as pentafluorophenyl esters. When this material was deprotected (TFA, anisole) and slowly added to iPr$_2$NEt/THF, it dimerized to 9 in 39% yield. Alternatively, 9 could be prepared in a single step (13% yield) by simply mixing commercially available A acid trichloride and B at 3 mM concentration with iPr$_2$NEt in dry THF.

$^1$H NMR titrations in CDCl$_3$ showed that 9 formed 1:1 complexes with certain peptides and that N-Ac-L-Val-NHtBu was particularly well bound. To predict the structure of the most stable complex, a 5000-step MacroModel/SUMM conformational search (Goodman, J. M.; Still, W. C. *J. Comput. Chem.* 1991, 12, 1110) was carried out using AMBER*$^3$ and GB/SA chloroform (Still, W. C.; Tempczyk, A.; Hawley, R. C.; Hendrickson, T. *J. Am. Chem. Soc.* 1990 112, 6127. CHCl$_3$ parameter set: Hollinger, F.; Still, W. C., unpublished results). The most stable structure found is a complex held together by four intermolecular hydrogen bonds forming a structure resembling a peptidic three-strand β-sheet.

A related pair of intramolecular hydrogen bonds (between B's) closes the unbound end of 9 to produce a deep cavity which fully encapsulates the side chain (R) of a bound L-peptide. With L-valine, this structure places the side-chain isopropyl near the face of the four aromatic rings (A) of 9. It is incompatible with the $^1$H NMR of the corresponding L-valine methylamide complex, which shows a 2.5 ppm upfield shift for the side-chain methyls and an ~1 ppm downfield shift of only one of the three different types of host NH's.

The picture which emerges from association energy measurements (Table II) is also in accord with the binding mode described supra which projects L-amino acid side chains into the central cavity of the receptor.

TABLE II

| | Binding Energies (Kcal/mol) of Receptor 9 and Peptides$^a$ | | | |
|---|---|---|---|---|
| entry | peptide | −ΔG(L) | −Δ(D) | ΔΔ$_G^b$ (% ee) |
| 1 | N—Ac—Gly—NHMe | 1.9 | | |
| 2 | N—Ac—Ala—NHMe | 3.5 | 2.2 | 1.3 (80) |
| 3 | N—Ac—Val—NHMe | 5.0 | 2.4 | 2.6 (97) |
| 4 | N—Ac—Ile—NHMe | 4.3 | 2.4 | 1.9 (92) |
| 5 | N—Ac—Leu—NHMe | 3.4 | 2.4 | 1.0 (68) |
| 6 | N—Ac—Pgly$^c$—NHMe | 5.9 | 2.9 | 3.0 (>99) |
| 7 | N—Ac—Phe—NHMe | NC$^d$ | 2.0 | >−2.0 (.93) |
| 8 | N—Oc$^e$—Tyr—NHMe | NC$^d$ | | |
| 9 | N—Ac—Ser—NHMe | 3.5 | 3.4 | 0.1 (8) |
| 10 | N—Ac—HSer$^f$—NHMe | 5.1 | 3.7 | 1.4 (83) |
| 11 | N—Ac—Thr—NHMe | 3.5 | 2.9 | 0.6 (46) |
| 12 | N—Boc—Val—NHMe | 2.8 | 1.7 | 1.1 (70) |
| 13 | N—Boc—Val—NH$_2$ | 4.9 | 3.7 | 1.2 (76) |
| 14 | N—Boc—Gly—Val—NHMe | 6.2 | 3.2 | 3.0 (>99) |
| 15 | N—Boc—Gly—Val—Gly—NHBn | >7.2 | 4.6 | >2.6 (>97) |

$^a$By NMR titration at 25° C. of 0.5 mM 9 in CDCl$_3$ (each binding energy is the average of two to five independent measurements on different protons, and the average of two to five independent measurements on different protons, and the largest deviation from the average is ≦0.2 kcal/mol).
$^b$Enantioselectivity favoring L.
$^c$PGly, phenylglycine.
$^d$NC, no complex observed.
$^e$Oc, octanoyl.
$^f$HSer, homoserine.

Thus peptide derivatives are bound with high selectivity for the L-configuration except when side chains are large (entries 7 and 8). Valine and phenylglycine side chains appear to fit the binding cavity quite well, but substantial reductions in binding occur when even single methylenes are added (entries 3 vs 4 and 5 and 6 vs 7 and 8). Removal of side-chain bulk from a near-optimal side chain (iPR) also diminishes binding. Thus stepwise truncation of side-chain iPR to Me to H costs 1.5 kcal/mol per step with L-amino acids. The effect is less significant with D-amino acids, which the model suggests to have side chains projecting away from the binding site and into solvent. Finally, the large binding energies in entries 14 and 15 suggest that 9 can interact associatively with as many as three residues, a feat that appears unique among synthetic receptors. Presumably, the terminal residues of such peptides are able to form additional hydrogen bonds to the outlying amides of the host (NHCO and CONH in the schematic).

Thus it is possible to assemble a large, conformationally well-defined receptor with remarkable binding properties starting from a few conformationally restricted subunits and well-known synthetic operations. There are doubtless many other such readily accessible heterooligomeric assemblies which have structural and binding properties analogous to those associated with macromolecular receptors.

III

The $A_4B_6$ macrotricycle described herein is remarkable for several reasons. First, it self-assembles in a single step from two commercially available materials, benzene-1,3,5-tricarbonyl trichloride and the diamine (1R2R)-diaminocyclohexane. Though the yield of this extraordinary reaction is only 13%, the receptor is readily isolated because it is the most chromatographically mobile of the product formed. Second, $A_4B_6$ is a highly selective receptor for neutral peptides. For example, it binds derivatives of L amino acids with enantioselectivities as high as 99% ee and can also distinguish between peptides based on the steric requirements of their sidechains. In some cases, this sidechain selectivity can be quite large and exceed 3 kcal/mol even when the peptides being compared differ only by a single methylene (e.g. phenylglycine vs phenylalanine). In the $A_4B_6$ receptor, the conformationally rigid building blocks used minimize its flexibility. The synthesis and properties of two related $A_4B_6$ cyclooligomers which are constructed from more conformationally flexible acyclic diamines (1R, 2R)-1,2-diphenylethylenediamine (hereinafter B1) and (2R, 3R)-2,3-diaminobutane-1,4-diol (hereinafter B2). The binding properties in this series of receptors are sensitive to the structure of the components used to assemble them, but rigid cyclic building blocks need not be used to obtain high binding selectivity.

To prepare the receptors, a simple one-step coupling was performed on the amines and the triacid chloride as described for $A_4B_6$. With B1, the $A_4B1_6$ receptor was obtained in 10% yield when the coupling was carried out at a concentration corresponding to 6 nM in receptor.

Synthesis of $A_4B1_6$: To an ice cold solution of (1R,2R)-diphenylethylenediamine (66 mg, 0.31 mmol) and $IPr_2NEt$ (0.16 mL, 0.63 mmol) in THF (100 mL) and dimethylacetamide (10 mL) was added 1,3,5-benzenetricarbonyl trichloride (55 mg, 0.21 mmol) as a single portion with stirring. After 2 hours at 0° C., the mixture was allowed to warm to room temperature and then to stand for an additional 12 hours. Volatile materials were removed at reduced pressure and the crude product was purified by flash chromatography on silica gel (3% methanol in methylene chloride). $A_4B1_6$ was the most mobile compound chromatographically and was isolated as an amorphous white solid (9.8 mg, 10%); TLC (5% MeOH in $CH_2Cl_2$) $R_f$=0.71; $^1$H NMR ($CDCl_3$) δ9.03 (d, 1H, J=5.2 Hz), 8.57 (d, 1H, J=9.2 Hz), 8.47 (s, 1H), 8.27 (s, 1H), 7.70 (s, 1H), 7.46–7.12 (m, 15H), 6.81 (m, 1H), 5.60 (m, 2H), 5.38 (dd, 1H, J=10.7, 6.9 Hz); $^{13}$C NMR ($CDCl_3$) δ168.7, 165.8, 164.7, 141.8–128.5 (m), 64.7, 62.8, 60.0; IR (neat) 3345, 2933, 1652, 1538, 1321 $cm^{-1}$; MS(FAB) m/z 1899 (M+1).

With B2, a more dilute 1 mM concentration was used to prepare $A_4B2_6$ in 7% yield. Both products were readily isolated as the most mobile reaction product on silica gel and were identified by mass spectroscopy and by their symmetry as revealed by $^{13}$C and $^1$H NMR.

Binding energies were measured by titrating 0.5 mM solutions of receptor in $CDCl_3$ with various N-acetyl amino acid methylamides and monitoring the receptor protons by 400 MHz NMR. In general, signals which showed the largest shifts upon binding were certain aromatic (H—C) and amide (H—N) protons. The binding energies found are given in Table III and all represent averages of at least two different binding measurements. Scatchard treatment of binding data indicated 1:1 complexes in all cases.

TABLE III

Peptide-Binding Properties of Macrotricyclic Receptors in $CDCl_3$.

| Peptide Substrate[a] | $A_4B_6$ | | $A_4B1_6$ | | $A_4B2_6$ | |
|---|---|---|---|---|---|---|
| | −ΔG[b] | ΔΔG[c] | −ΔG[b] | ΔΔG[c] | −ΔG[b] | ΔΔG[c] |
| GLY | 1.9[d] | | 1.4 | | 1.5 | |
| L—ALA | 3.5 | 1.3 (80% ee) | 4.1 | 1.8 (90% ee) | 3.7 | 1.7 (89% ee) |
| D—ALA | 2.2 | | 2.3 | | 2.0 | |
| L—VAL | 5.0 | 2.8 (98% ee) | 4.5 | 2.4 (98% ee) | 3.8 | 1.5 (84% ee) |
| D—VAL | 2.4 | | 2.1 | | 2.3 | |
| L—ILE | 4.3 | 1.9 (92% ee) | 4.2 | 2.2 (95% ee) | 2.6 | 0.4 (32% ee) |
| D—ILE | 2.4 | | 2.0 | | 2.2 | |
| L—LEU | 3.4 | 1.0 (68% ee) | 3.6 | 1.5 (84% ee) | 2.5 | 0.3 (24% ee) |
| D—LEU | 2.4 | | 2.1 | | 2.2 | |
| L—PHE | NC | — | NC | — | NC | — |
| D—PHE | 2.0 | | 1.5 | | 1.4 | |
| L—Phenylglycine | 5.9 | 3.0 (>99% ee) | 5.7 | 3.9 (>99% ee) | 3.4 | 1.6 (87% ee) |
| D—Phenylglycine | 2.9 | | 1.8 | | 1.8 | |
| L—Ethylglycine | 5.7 | 3.3 (>99% ee) | 5.5 | 3.4 (>99% ee) | 5.5 | 3.3 (>99% ee) |
| D—Ethylglycine | 2.4 | | 2.1 | | 2.2 | |
| L—Propylglycine | 6.0 | 3.5 (>99% ee) | 5.7 | 3.5 (>99% ee) | 4.8 | 2.5 (97% ee) |
| D—Propylglycine | 2.5 | | 2.2 | | 2.3 | |
| L—Butylglycine | 3.9 | 1.4 (82% ee) | 3.8 | 1.8 (87% ee) | 2.5 | 0.2 (16% ee) |
| D—Butylglycine | 2.5 | | 2.2 | | 2.3 | |

[a]All peptides are N-acetyl, methylamides;
[b]binding energy (kcal/mol);
[c]enantioselectvity (kcal/mol);
NC = no complexation observed.

Figure 2:
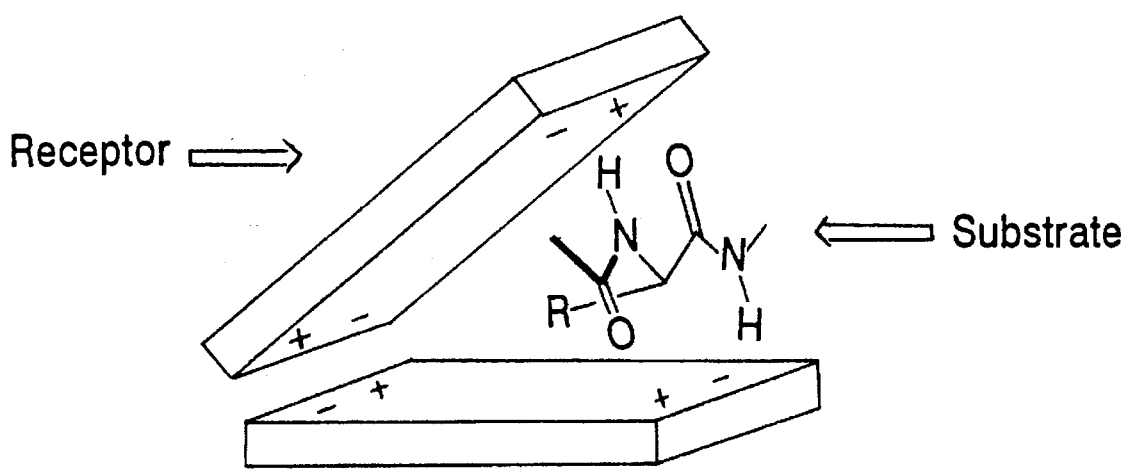
FIG. 2 shows a diagram of a model for receptor-substrate binding.

The binding results obtained with all three receptors support the general picture of the complex shown in FIG. 2. In the diagram, '+' and '−' represent receptor hydrogen bond donors (H—N) and acceptors (O═C), respectively. These functionalities presumably not only bind the peptidic substrate by hydrogen bonds but also associate to close the other end of the receptor to create a conical binding cavity which can encapsulate the sidechain (R) of a bound L amino acid.

The binding data in Table III reveals a number of notable trends. First, all receptors bind all D amino acid substrates with roughly the same binding energy (2.0–2.5 kcal.mol). Thus the high enantioselectivities observed originate from especially favorable binding to L peptide substrates, not by destabilization of binding to D substrates. Second, both the $A_4B_6$ receptor and the $A_4B1_6$ analog have similar binding selectivities despite the construction of the latter from an acyclic diamine. Indeed, $A_4B1_6$ binds six of the eight substrates studied with higher enantioselectivity than does $A_4B_6$.

Both $A_4B_6$ and $A_4B1_6$ show surprisingly high selectivity among L amino acids which are distinguished only by the size and shape of their unfunctionalized, hydrocarbon sidechains. Amino acids having branched sidechains bind well only when the branch occurs at the substrate β-carbon. Thus valine and isoleucine (R=i-Pr, s-Bu) bind well but leucine (R=i-Bu) does not. The receptors also distinguish substrates by sidechain length. Thus while alanine and butylglycine (R=Me, n-Bu) are rather poorly bound, ethylglycine and propylglycine (R=Et, n-Pr) are among the best substrates. All three receptors distinguish phenylglycine and phenylalanine by >3 kcal/mol. These observations are compatible with the conical-cavity model which favors substrates having more steric bulk near the enlarged, open end of the binding cavity. Substrates with sidechains that are either too small to fill the cavity or too long to be accommodated are poorly bound. While binding selectivity based on steric effects is known (For example see: F. Diederich, K. Dick and D. Griebel, *J. Am. Chem. Soc.*, 108, 2273 (1986); W. L. Mock and N.-Y. Shih, *J. Am. Chem. Soc.*, 110, 4706 (1988); M. A. Petti, T. J. Shepodd, R. E. Barrans and D. A. Dougherty, *J. Am. Chem. Soc.*, 110, 6825 (1988); D. J. Cram, M. E. Tanner, S. J. Kelpert and C. B. Knobler, *J. Am. Chem. Soc.*, 113, 8909 (1991); K. Naemura, K. Ueno, S. Takeuchi, Y. Tobe, T. Kaneda and Y. Sakata, *J. Am. Chem. Soc.*, 115, 8475 (1993); L. Garle, B. Lozach, J.-P. Dutasta and A. Collet, *J. Am. Chem. Soc.*, 115, 11652 (1993)), the subtle differences in sidechain bulk which these receptors are able to distinguish energetically by 1–2 kcal/mol is unusual with synthetic receptors. The key to such high steric selectivity appears to coincide with the receptor's ability to fully encapsulate the chemical substructure being distinguished.

Like $A_4B_6$ and $A_4B1_6$ which bind L-peptides based on the steric requirements of their sidechains, receptor $A_4B2_6$ also distinguishes peptide sidechains sterically but with different selectivity. In particular, $A_4B2_6$ selects for L-peptides whose sidechains are small and compact; thus alanine, valine and ethylglycine are well-bound while isoleucine, leucine, phenylglycine, propylglycine and butylglycine are more weakly bound relative to the other receptors. Thus $A_4B2_6$ appears to have a smaller binding cavity, a property which may follow from cavity occupancy by benzyloxymethyl substituents or from partial cavity collapse due to the flexible nature of the B2 fragment.

These findings suggest that the highly selective binding found with the $A_4B_6$ receptor may be general to cyclooligomeric molecules of this class and that binding selectivity can be altered by starting with different amine and acid chloride fragments. It may be noted that these receptors incorporate diamine fragments in two different structural environments: the upper and lower macrocycles include four equivalent amines B while two other B's link those macrocycles together. By varying these distinct B fragments independently, even more receptor diversity can be generated.

What is claimed is:

1. A composition of matter having the structure:

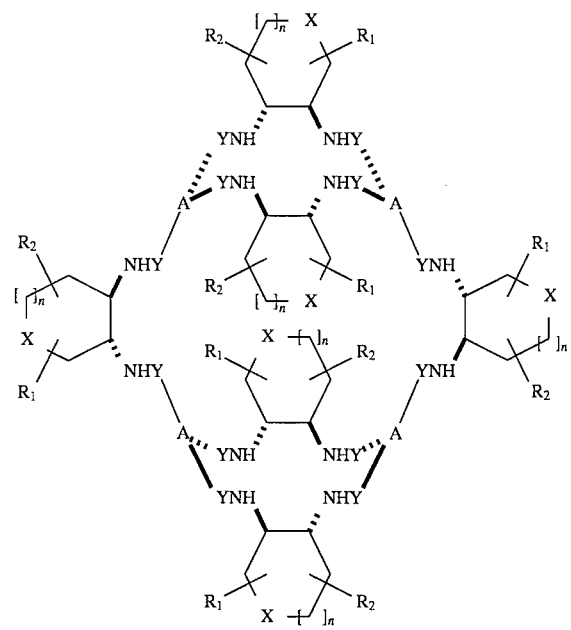

wherein A has the structure:

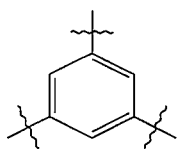

and $R_1$ and $R_2$ are independently the same or different and are H, F, a linear or branched chain alkyl, arylalkyl, alkoxyalkyl, aminoalkyl, alkylaminoalkyl, hydroxyalkyl, (cycloalkyl)alkyl, or acylalkyl group, or an aryl group, a linear or branched chain alkylaryl, pyridyl, thiophene, pyrrolyl, indolyl or naphthyl group; X is $CH_2$ or NH; Y is C=O or $SO_2$; and n is 0 to about 3.

2. The composition of claim 1 wherein X is NH.

3. The composition of claim 1 wherein X is $CH_2$, Y is C=O and n is 1.

4. The composition of claim 3 wherein $R_1$ and $R_2$ are H.

* * * * *